US010117639B2

(12) United States Patent
Yamada et al.

(10) Patent No.: US 10,117,639 B2
(45) Date of Patent: Nov. 6, 2018

(54) ULTRASONIC SENSOR AS WELL AS PROBE AND ELECTRONIC APPARATUS

(71) Applicant: SEIKO EPSON CORPORATION, Tokyo (JP)

(72) Inventors: Masayoshi Yamada, Nagano (JP); Hiroshi Matsuda, Gifu (JP); Tomoaki Nakamura, Nagano (JP); Hiroshi Ito, Nagano (JP); Hiromu Miyazawa, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 625 days.

(21) Appl. No.: 14/869,094

(22) Filed: Sep. 29, 2015

(65) Prior Publication Data

US 2016/0089111 A1    Mar. 31, 2016

(30) Foreign Application Priority Data

Sep. 30, 2014 (JP) .................. 2014-201934

(51) Int. Cl.
*G01N 29/24* (2006.01)
*A61B 8/00* (2006.01)
(Continued)

(52) U.S. Cl.
CPC .......... *A61B 8/4483* (2013.01); *A61B 8/4427* (2013.01); *A61B 8/4444* (2013.01); *A61B 8/4488* (2013.01); *A61B 8/4494* (2013.01); *A61B 8/462* (2013.01); *B06B 1/0629* (2013.01); *G01N 29/0654* (2013.01); *G01N 29/226* (2013.01); *G01N 29/2437* (2013.01);
(Continued)

(58) Field of Classification Search
CPC ... A61B 8/4483; A61B 8/4494; A61B 8/4427; A61B 8/4444; A61B 8/4488; A61B 8/462; G01N 29/2437; G01N 29/0654; G01N 29/226; G01N 2291/02475; G01N 2291/106; H01L 41/1138
See application file for complete search history.

(56) References Cited

U.S. PATENT DOCUMENTS

| | | | | |
|---|---|---|---|---|
| 6,389,877 B1 * | 5/2002 | Takeuchi | ................. | G01G 3/16 73/19.03 |
| 2010/0148627 A1 | 6/2010 | Funasaka et al. | | |

(Continued)

FOREIGN PATENT DOCUMENTS

| | | |
|---|---|---|
| JP | 2000-183413 A | 6/2000 |
| JP | 2010-165341 A | 7/2010 |

(Continued)

*Primary Examiner* — Elmer Chao

(57) ABSTRACT

An ultrasonic sensor includes a vibration plate, a first electrode, a piezoelectric body, and a second electrode. The first electrode is laminated on the vibration plate, that has a length along a surface of the vibration plate in a first direction, and that has a width Wbe along the surface of the vibration plate in a second direction that is orthogonal to the first direction. The width Wbe is not more than the length. The piezoelectric body is laminated on the first electrode and has a width Wpz in the second direction. The second electrode is laminated on the piezoelectric body. A ratio Wbe/Wpz between the width Wbe of the first electrode and the width Wpz of the piezoelectric body is not less than 0.1 and not more than 0.8.

10 Claims, 24 Drawing Sheets

(51) Int. Cl.
*B06B 1/06* (2006.01)
*G01N 29/06* (2006.01)
*G01N 29/22* (2006.01)
*H01L 41/113* (2006.01)

(52) U.S. Cl.
CPC ............ *H01L 41/1138* (2013.01); *G01N 2291/02475* (2013.01); *G01N 2291/106* (2013.01)

(56) References Cited

U.S. PATENT DOCUMENTS

| | | |
|---|---|---|
| 2010/0202253 A1 | 8/2010 | Nakamura |
| 2011/0115337 A1 | 5/2011 | Nakamura et al. |
| 2011/0141047 A1 | 6/2011 | Iwaizumi et al. |
| 2011/0221306 A1 | 9/2011 | Matsuda |

FOREIGN PATENT DOCUMENTS

| | | |
|---|---|---|
| JP | 2010-183437 A | 8/2010 |
| JP | 2011-124973 A | 6/2011 |
| JP | 2011-210283 A | 10/2011 |
| JP | 2011-211164 A | 10/2011 |

\* cited by examiner

ULTRASONIC SENSOR AS WELL AS PROBE AND ELECTRONIC APPARATUS

CROSS-REFERENCE TO RELATED APPLICATIONS

This application claims priority to Japanese Patent Application No. 2014-201934 filed on Sep. 30, 2014. The entire disclosure of Japanese Patent Application No. 2014-201934 is hereby incorporated herein by reference.

BACKGROUND

Technical Field

The present invention relates to an ultrasonic sensor as well as a probe, an electronic apparatus, an ultrasonic imaging apparatus, and the like using the same.

Related Art

Ultrasonic devices for use in ultrasonic diagnostic apparatuses, for example, are commonly known. Ultrasonic devices include a vibration plate. A bottom electrode is laminated on the vibration plate. A piezoelectric body is laminated on the bottom electrode. A top electrode is laminated on the piezoelectric body. The piezoelectric body extends to the outside of the outline of the bottom electrode, thereby preventing short-circuiting between the top electrode and the bottom electrode.

JP-A-2000-183413 discloses a displacement element. The displacement element includes a piezoelectric element that is laminated on a vibration plate. The ratio of the width of the piezoelectric element to the width of the vibration plate is specified. Thus, optimization of the displacement with respect to the driving voltage is proposed. However, in JP-A-2000-183413, no mention is made of the potential that is output when the vibration plate is displaced. Moreover, the width of the piezoelectric film and the width of the electrode are the same as each other. Therefore, the effect of the width of the bottom electrode with respect to the thickness of the piezoelectric film is not considered at all.

SUMMARY

In accordance one aspect of the invention, an ultrasonic sensor includes a vibration plate, a first electrode, a piezoelectric body, and a second electrode. The first electrode is laminated on the vibration plate, and the first electrode has a length along a surface of the vibration plate in a first direction and a width Wbe along the surface of the vibration plate in a second direction that is orthogonal to the first direction. The width Wbe is not more than the length. The piezoelectric body is laminated on the first electrode and has a width Wpz in the second direction. The second electrode is laminated on the piezoelectric body. A ratio Wbe/Wpz between the width Wbe of the first electrode and the width Wpz of the piezoelectric body is not less than 0.1 and not more than 0.8.

According to the aspect of the invention, the ratio Wbe/Wpz is not more than 0.5.

According to the aspect of the invention, in a plan view that is orthogonal to the surface of the vibration plate, a distance from an outline of the piezoelectric body to an outline of the vibration plate in the second direction is not less than 0.02 times and not more than 0.3 times a width of the vibration plate.

According to the aspect of the invention, in the first direction, the second electrode has a smaller width than the piezoelectric body.

According to the aspect of the invention, an aspect ratio Lcav/Wcav between a width Wcav of the vibration plate in the second direction and a length Lcav of the vibration plate in the first direction is not less than 1 and not more than 2.

According to the aspect of the invention, in a plan view that is orthogonal to the surface of the vibration plate, an area of overlap between the second electrode and the first electrode is within a range of not less than 1% and not more than 20% with respect to an area of the vibration plate that is defined by an outline of the vibration plate in the plan view.

According to the aspect of the invention, an outline of the vibration plate has one of a circular shape, a hexagonal shape, and an elliptical shape.

In accordance another aspect of the invention, a probe includes the ultrasonic sensor according to the aspect of the invention, and a housing that supports the ultrasonic sensor.

In accordance another aspect of the invention, an electronic apparatus includes the ultrasonic sensor according to the aspect of the invention, and a processor connected to the ultrasonic sensor and configured to process an output from the ultrasonic sensor.

In accordance another aspect of the invention, an ultrasonic imaging apparatus, includes the ultrasonic sensor according to the aspect of the invention, and a display device configured to display an image generated based on an output from the ultrasonic sensor.

BRIEF DESCRIPTION OF THE DRAWINGS

Referring now to the attached drawings which form a part of this original disclosure.

DETAILED DESCRIPTION OF EXEMPLARY EMBODIMENTS

The following describes embodiments of the invention with reference to the attached drawings. It should be noted that the embodiments to be described hereinafter are not intended to unduly limit the scope of the invention defined by the claims and that not all of the configurations to be described in the embodiments are necessarily essential as the means for achieving the invention.

(1) Overall Configuration of Ultrasonic Diagnostic Apparatus

Figure 1:
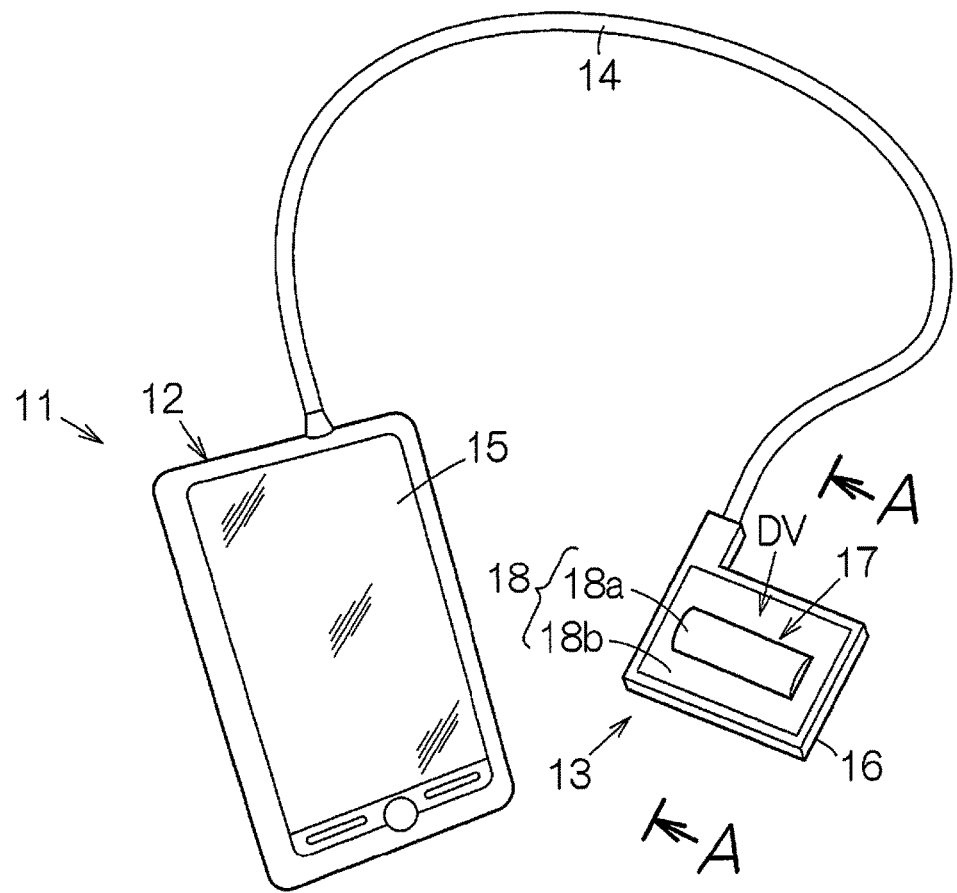
FIG. 1 is an external view schematically showing a specific example, that is, an ultrasonic diagnostic apparatus, of an electronic apparatus according to an embodiment.

FIG. 1 schematically shows the configuration of a specific example, that is, an ultrasonic diagnostic apparatus (ultrasonic imaging apparatus) 11, of an electronic apparatus according to an embodiment of the invention. The ultrasonic diagnostic apparatus 11 includes a device terminal (processing unit) 12 and an ultrasonic probe (probe) 13. The device terminal 12 and the ultrasonic probe 13 are connected to each other via a cable 14. Electric signals are transmitted through the cable 14 between the device terminal 12 and the ultrasonic probe 13. A display panel (display device) 15 is incorporated into the device terminal 12. A screen of the display panel 15 is exposed at a surface of the device terminal 12. In the device terminal 12, an image is generated based on ultrasonic waves detected by the ultrasonic probe 13. The imaged detection result is displayed on the screen of the display panel 15.

The ultrasonic probe 13 has a housing 16. An ultrasonic device unit DV is fitted in the housing 16. The ultrasonic device unit DV includes an ultrasonic device (ultrasonic sensor) 17. The ultrasonic device 17 includes an acoustic lens 18. A partial cylindrical surface 18a is formed on an outer surface of the acoustic lens 18. The partial cylindrical surface 18a is surrounded by a flat plate portion 18b. The entire outer perimeter of the flat plate portion 18b is continuously joined to the housing 16. Thus, the flat plate portion 18b functions as a portion of the housing. The acoustic lens 18 may be formed of, for example, a silicone resin. The acoustic lens 18 has an acoustic impedance that is similar to the acoustic impedance of a living body. The ultrasonic device 17 outputs ultrasonic waves from its surface and receives reflected waves of the ultrasonic waves.

(2) Structure of Ultrasonic Device

Figure 2:
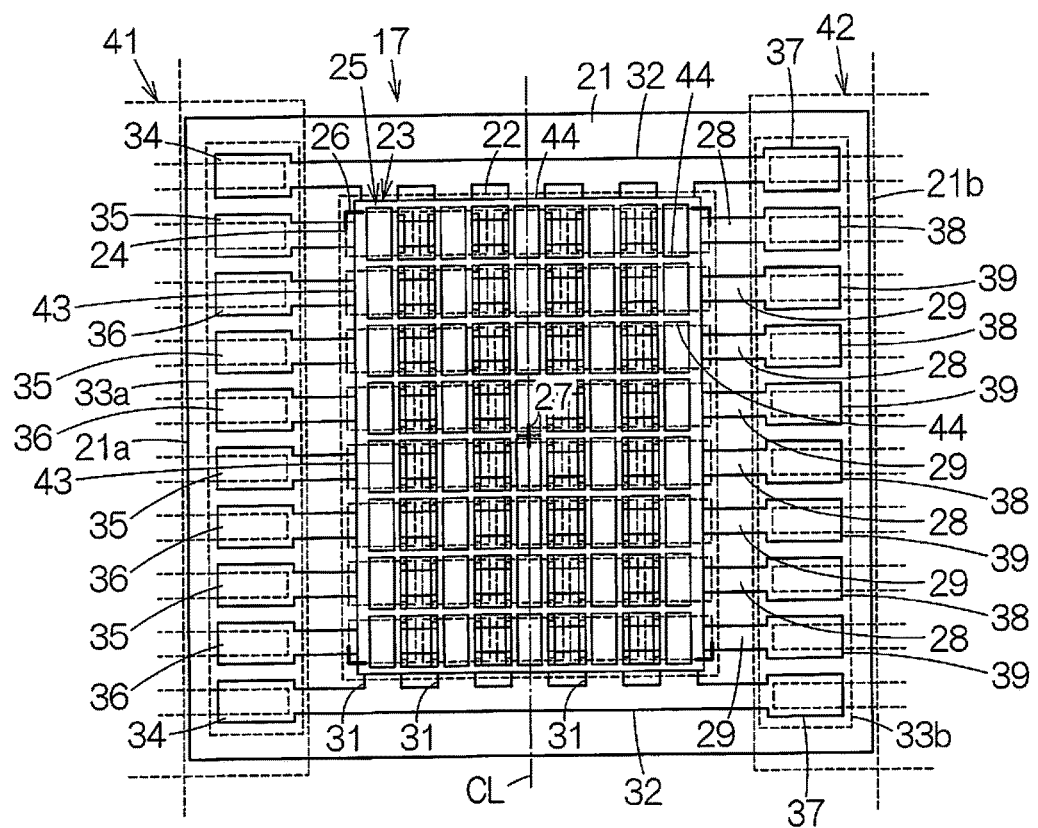
FIG. 2 is an enlarged plan view of an ultrasonic device.

FIG. 2 schematically shows a plan view of the ultrasonic device 17 according to the embodiment. The ultrasonic device 17 includes a base 21. An element array 22 is formed on the base 21. The element array 22 is constituted by an arrangement of ultrasonic transducer elements (hereinafter referred to as "elements") 23. The arrangement is in the form of a matrix having a plurality of columns and a plurality of rows. Moreover, in the arrangement, a staggered arrangement may also be established. In a staggered arrangement, a group of elements 23 in each even row can be displaced relative to a group of elements 23 in each odd row by one-half of the column pitch. Either the number of elements in each odd row or the number of elements in each even row may be smaller than the other by one.

Each element 23 includes a vibration plate 24. Details of the vibration plate 24 will be described later. In FIG. 2, the outline of the vibration plate 24 when viewed from above in a direction orthogonal to the film surface of the vibration plate 24 (when viewed from above in a thickness direction of a substrate) is shown by dashed lines. The inside of the outline corresponds to the inside of the region of the vibration plate 24. The outside of the outline corresponds to the outside of the region of the vibration plate 24. A piezoelectric element 25 is formed on the vibration plate 24. In the piezoelectric element 25, a piezoelectric film is sandwiched between a top electrode and a bottom electrode as described later. These are sequentially laid one on top of another.

The element array 22 defines an element array region 26. The outline of the element array region 26 is formed by a minimum-area quadrilateral circumscribing the vibration plates 24 that are located at the outermost perimeter. When viewed from above, a centroid 27 of the outline lies on a center line CL of the element array 22. The element array 22 can be formed line-symmetrically with respect to the center line CL, for example. The ultrasonic device 17 is configured as a single ultrasonic transducer element chip (substrate).

A plurality of first electric conductors 28 are formed on the surface of the base 21. The first electric conductors 28 extend parallel to one another in a row direction of the arrangement. One first electric conductor 28 is assigned to corresponding one row of elements 23. One first electric conductor 28 is disposed in common for the elements 23 that are lined up in the row direction of the arrangement. The first electric conductor 28 forms bottom electrodes for the respective elements 23. In this manner, the first electric conductor 28 is disposed inside and outside the regions of the vibration plates 24. A transmission row of elements 23 is formed for each first electric conductor 28. For example, a laminated film of titanium (Ti), iridium (Ir), platinum (Pt), and titanium (Ti) can be used for the first electric conductors 28. However, other electrically conductive materials may also be used for the first electric conductors 28.

A plurality of second electric conductors 29 are formed on the surface of the base 21. The second electric conductors 29 extend parallel to one another in the row direction of the arrangement. One second electric conductor 29 is assigned to corresponding one row of the elements 23. One second electric conductor 29 is disposed in common for the elements 23 that are lined up in the row direction of the arrangement. The second electric conductor 29 forms bottom electrodes for the respective elements 23. In this manner, the second electric conductor 29 is disposed inside and outside the regions of the vibration plates 24. A receiving row of elements 23 is formed for each second electric conductor 29. At least one receiving row is combined with each transmission row. Here, the transmission rows and the receiving rows are arranged alternately in a column direction. For example, a laminated film of titanium (Ti), iridium (Ir), platinum (Pt), and titanium (Ti) can be used for the second electric conductors 29. However, other electrically conductive materials may also be used for the second electric conductors 29.

A plurality of third electric conductors 31 are formed on the surface of the base 21. The third electric conductors 31 extend parallel to one another in the column direction of the arrangement. One third electric conductor 31 is assigned to corresponding one column of elements 23. One third electric conductor 31 is connected in common to the elements 23 that are lined up in the column direction of the arrangement. The third electric conductor 31 forms top electrodes for the respective elements 23. The two ends of each third electric conductor 31 are respectively connected to a pair of extraction interconnects 32. The extraction interconnects 32 extend parallel to each other in the row direction of the arrangement. Therefore, all the third electric conductors 31 have the same length. Thus, the top electrodes are connected in common to the elements 23 of the entire matrix. In this manner, the third electric conductors 31 are disposed inside and outside the regions of the vibration plates 24. The third electric conductors 31 can be formed of, for example, iridium (Ir). However, other electrically conductive materials may also be used for the third electric conductors 31.

Energization of the elements 23 is switched on a row-by-row basis. A linear scan and a sector scan can be achieved in accordance with this switching of energization. Since the elements 23 in a single row simultaneously output ultrasonic waves, the number of elements in a single row, that is, the number of columns of the arrangement can be determined in accordance with the output level of ultrasonic waves. The number of columns can be set at, for example, about 10 to 15. In FIG. 2, some columns are not shown, and only five columns are shown. The number of rows of the arrangement can be determined in accordance with the extent of the scan range. The number of rows can be set at, for example, 128 or 256. In FIG. 2, some rows are not shown, and only eight rows are shown. The functions of the top electrodes and the bottom electrodes may be reversed. That is to say, it is also possible that while the bottom electrodes are connected in common to the elements 23 of the entire matrix, the top electrodes are connected in common to the elements 23 in each row of the arrangement.

The outline of the base 21 has a first side 21a and a second side 21b that are defined by a pair of mutually parallel straight lines and that oppose each other. A first terminal array 33a in a single line is disposed between the first side 21a and the outline of the element array 22. A second terminal array 33b in a single line is disposed between the second side 21b and the outline of the element array 22. The first terminal array 33a can form a single line parallel to the first side 21a. The second terminal array 33b can form a single line parallel to the second side 21b.

The first terminal array 33a is constituted by a pair of top electrode terminals 34 as well as first bottom electrode terminals 35 and second bottom electrode terminals 36. The top electrode terminals 34 are arranged at opposite ends of the first terminal array 33a. The extraction interconnects 32 are connected to the respective top electrode terminals 34. In this manner, all the elements 23 are connected in common to the top electrode terminals 34. The first bottom electrode terminals 35 and the second bottom electrode terminals 36 are arranged between the top electrode terminals 34. The first bottom electrode terminals 35 are connected to the respective first electric conductors 28, and the second bottom electrode terminals 36 are connected to the respective second electric conductors 29. In this manner, the elements 23 of each transmission row are connected to a corresponding first bottom electrode terminal 35. The elements 23 of each receiving row are connected to a corresponding second bottom electrode terminal 36.

Similarly, the second terminal array 33b is constituted by a pair of top electrode terminals 37 as well as third bottom electrode terminals 38 and fourth bottom electrode terminals 39. The top electrode terminals 37 are arranged at opposite ends of the second terminal array 33b. The extraction interconnects 32 are connected to the respective top electrode terminals 37. In this manner, all the elements 23 are connected in common to the top electrode terminals 37. The third bottom electrode terminals 38 and the fourth bottom electrode terminals 39 are arranged between the top electrode terminals 37. The third bottom electrode terminals 38 are connected to the respective first electric conductors 28, and the fourth bottom electrode terminals 39 are connected to the respective second electric conductors 29. In this manner, the elements 23 of each transmission row are connected to a corresponding third bottom electrode terminal 38, and the elements 23 of each receiving row are connected to a corresponding fourth bottom electrode terminal 39.

A first flexible printed wiring board (hereinafter referred to as "first wiring board") 41 is connected to the base 21. The first wiring board 41 covers the first terminal array 33a. Electrically conductive lines, namely, first signal lines are formed at one end of the first wiring board 41, individually corresponding to the top electrode terminals 34 and the first and second bottom electrode terminals 35 and 36. The first signal lines are individually opposed to the top electrode terminals 34 and the first and second bottom electrode terminals 35 and 36, and individually joined thereto.

Similarly, a second flexible printed wiring board (hereinafter referred to as "second wiring board") 42 is connected to the base 21. The second wiring board 42 covers the second terminal array 33b. Electrically conductive lines, namely, second signal lines are formed at one end of the second wiring board 42, individually corresponding to the top electrode terminals 37 and the third and fourth bottom electrode terminals 38 and 39. The second signal lines are individually opposed to the top electrode terminals 37 and the third and fourth bottom electrode terminals 38 and 39, and individually joined thereto.

Electrode separation films 43 are arranged, on the vibration plates 24, in parallel with the third electric conductors 31. The electrode separation films 43 extend in a longitudinal direction of the third electric conductors 31 so as to have strip shapes. The electrode separation films 43 have insulating ability and moisture-proofness. The electrode separation films 43 may be formed of, for example, a moisture-proof insulating material such as alumina ($Al_2O_3$) or silicon oxide ($SiO_2$). The electrode separation films 43 are formed separately on both sides of each third electric conductor 31 such that the third electric conductor 31 is sandwiched by the corresponding electrode separation films 43. Since the third electric conductors 31 cross the first electric conductors 28 and the second electric conductors 29 on the vibration plates 24, the electrode separation films 43, on the vibration plates 24, extend over and across the first electric conductors 28 and the second electric conductors 29.

On the base 21, insulating films 44 are formed outside the regions of the vibration plates 24. The insulating films 44 extend in a longitudinal direction of the first and second electric conductors 28 and 29 so as to have strip shapes. The insulating films 44 are arranged in parallel with the first and second electric conductors 28 and 29. The insulating films 44 may be formed of, for example, a moisture-proof insulating material such as alumina or silicon oxide. The material for the insulating films 44 may be the same as the material for the electrode separation films 43. The insulating films 44 extend over and across the third electric conductors 31. In this manner, the insulating films 44 are formed on the third electric conductors 31. The insulating films 44 are continuous with the electrode separation films 43. The insulating films 44 are connected to the electrode separation films 43, which are formed on both sides of each third electric conductor 31 such that the third electric conductor 31 is sandwiched by the corresponding electrode separation films 43.

Figure 3:
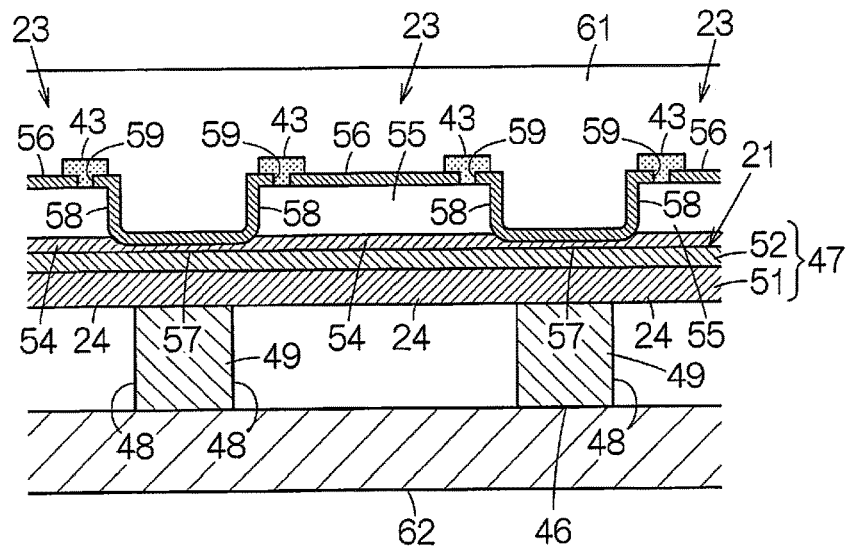
FIG. 3 is a cross-sectional view taken along line A-A in FIG. 1.

As shown in FIG. 3, the base 21 includes a substrate 46 and a coating film 47. The coating film 47 is laminated over the entire surface of the substrate 46. In the substrate 46, an opening 48 is formed for each of the elements 23. The openings 48 are arranged in an array in the substrate 46. The outline of a region where the openings 48 are arranged corresponds to the outline of the element array region 26. A partitioning wall 49 is disposed between every two adjacent openings 48. Adjacent openings 48 are separated from each other by the partitioning walls 49. The wall dimension of the partitioning walls 49 corresponds to the spacing between the openings 48. The substrate 46 can be formed of, for example, a silicon substrate.

The coating film 47 is composed of a silicon oxide ($SiO_2$) layer 51 that is laminated on the surface of the substrate 46 and a zirconium oxide ($ZrO_2$) layer 52 that is laminated on a surface of the silicon oxide layer 51. Portions of the coating film 47 that correspond to the respective outlines of the openings 48 form the vibration plates 24. The vibration plates 24 refer to those portions of the coating film 47 that face the respective openings 48 and that can thus perform film vibration in the thickness direction of the substrate 46. The film thickness of the silicon oxide layer 51 can be determined based on resonance frequency.

A bottom electrode 54, a piezoelectric film 55, and a top electrode 56 are sequentially laminated on the surface of each vibration plate 24. The piezoelectric film 55 can be formed of, for example, lead zirconate titanate (PZT). Other piezoelectric materials may also be used for the piezoelectric film 55. Here, each first electric conductor 28 has the bottom electrodes 54 and first electrically conductive films 57. The first electrically conductive films 57 are connected to the bottom electrodes 54. The first electrically conductive films 57 are continuous with the bottom electrodes 54. The film thickness of the first electrically conductive films 57 is smaller than the film thickness of the bottom electrodes 54. Second electrically conductive films 58 are connected to the first electrically conductive films 57. The second electrically conductive films 58 branch off from the first electrically conductive films 57, extend onto the piezoelectric films 55, and end at positions spaced apart from the top electrodes 56. Gaps 59 are formed on top surfaces of the piezoelectric films 55, each of the gaps 59 being located between a top electrode 56 and a corresponding second electrically conductive film 58.

As shown in FIG. 3, the electrode separation films 43 are each formed between a top electrode 56 and a corresponding second electrically conductive film 58. The electrode separation films 43 fill the gaps 59 on the top surfaces of the piezoelectric films 55. Thus, those portions of the surfaces of the piezoelectric films 55 that are each located between a top electrode 56 and a corresponding second electrically conductive film 58 are covered with the electrode separation films 43. Here, in the longitudinal direction of the first electric conductors 28, the electrode separation films 43 fit within the regions of the vibration plates 24. The electrode separation films 43 do not lie over the edges of the vibration plates 24.

An acoustic matching layer 61 is laminated over the surface of the base 21. The acoustic matching layer 61 covers the element array 22. The film thickness of the acoustic matching layer 61 is determined in accordance with the resonance frequency of the vibration plates 24. For example, a silicone resin film can be used for the acoustic matching layer 61.

The acoustic lens 18 is disposed on the acoustic matching layer 61. The acoustic lens 18 is in close contact with a surface of the acoustic matching layer 61. The acoustic matching layer 61 serves to allow the acoustic lens 18 to adhere to the base 21. The partial cylindrical surface 18a of the acoustic lens 18 has generating lines that are parallel to the third electric conductors 31. The curvature of the partial cylindrical surface 18a is determined in accordance with the focus position of ultrasonic waves emitted from a single row of elements 23 connected to a single first electric conductor 28. The acoustic lens 18 may be formed of, for example, a silicone resin. The acoustic lens 18 has an acoustic impedance that is similar to the acoustic impedance of a living body.

A backing material 62 is attached to the back surface of the base 21. The back surface of the base 21 is superposed on a surface of the backing material 62. The backing material 62 closes the openings 48 in the back surface of the ultrasonic device 17. The backing material 62 can be provided with a rigid base material. Herein, the partitioning walls 49 are coupled to the backing material 62 at their joint surfaces. The backing material 62 is joined to each partitioning wall 49 in at least one joint region. An adhesive can be used to join the backing material 62 to the partitioning walls 49.

(3) Operation of Ultrasonic Diagnostic Apparatus

Next, the operation of the ultrasonic diagnostic apparatus 11 will be briefly described. To transmit ultrasonic waves, a pulse signal is supplied to the piezoelectric elements 25 of the elements 23 in the transmission rows. The pulse signal is supplied to the elements 23 on a row-by-row basis through the first and third bottom electrode terminals 35 and 38 and the top electrode terminals 34 and 37. In each of the elements 23, an electric field acts on the piezoelectric film 55 between the bottom electrode 54 and the top electrode 56. The piezoelectric film 55 vibrates at the frequency of ultrasonic waves. The vibration of the piezoelectric film 55 is transferred to the vibration plate 24. Thus, the vibration plate 24 vibrates ultrasonically. As a result, a desired ultrasonic beam is emitted toward the subject (for example, the interior of a human body).

Reflected waves of the ultrasonic waves vibrate the vibration plate 24 of each of the elements 23 in the receiving rows. The ultrasonic vibration of the vibration plate 24 ultrasonically vibrates the piezoelectric film 55 at a desired frequency. A voltage is output from the piezoelectric element 25 in accordance with the piezoelectric effect of the piezoelectric film 55. In each of the elements 23, a voltage is generated between the top electrode 56 and the bottom electrode 54. The generated potentials are output from the second and fourth bottom electrode terminals 36 and 39 and the top electrode terminals 34 and 37 as electric signals. The ultrasonic waves are detected in this manner.

Ultrasonic waves are repeatedly transmitted and received. As a result, a linear scan or a sector scan is achieved. When the scan is completed, an image is formed based on digital signals of the output signals. The image thus formed is displayed on the screen of the display panel 15.

(4) Behavior of Thin-Film Ultrasonic Transducer Element

Figure 4:
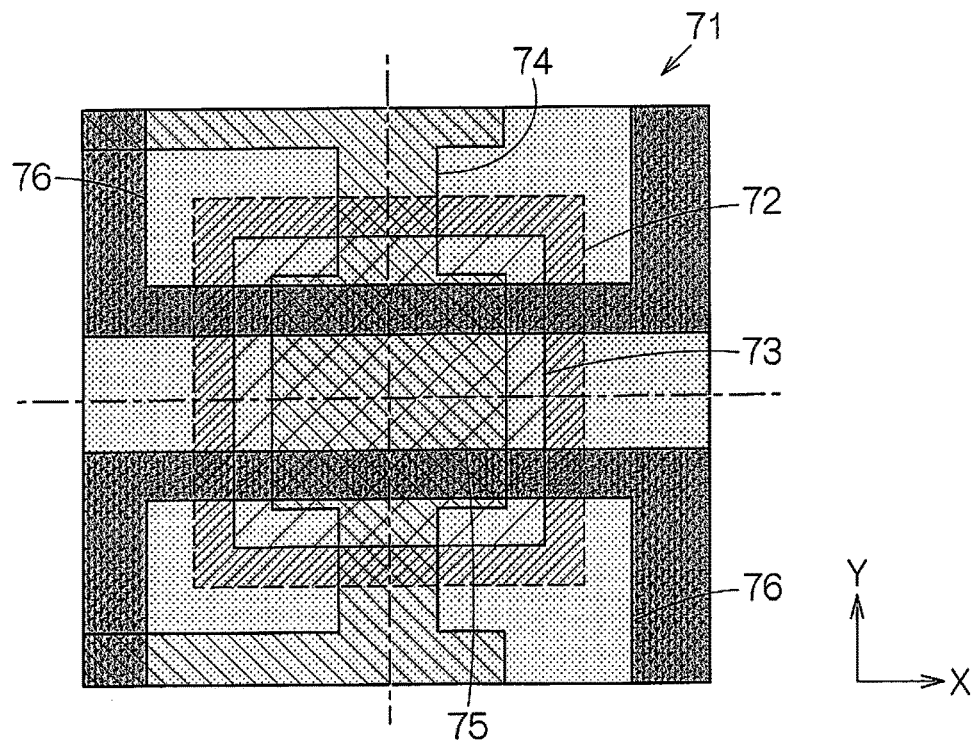
FIG. 4 is a conceptual diagram schematically showing the configuration of a simulation model.
Figure 5:
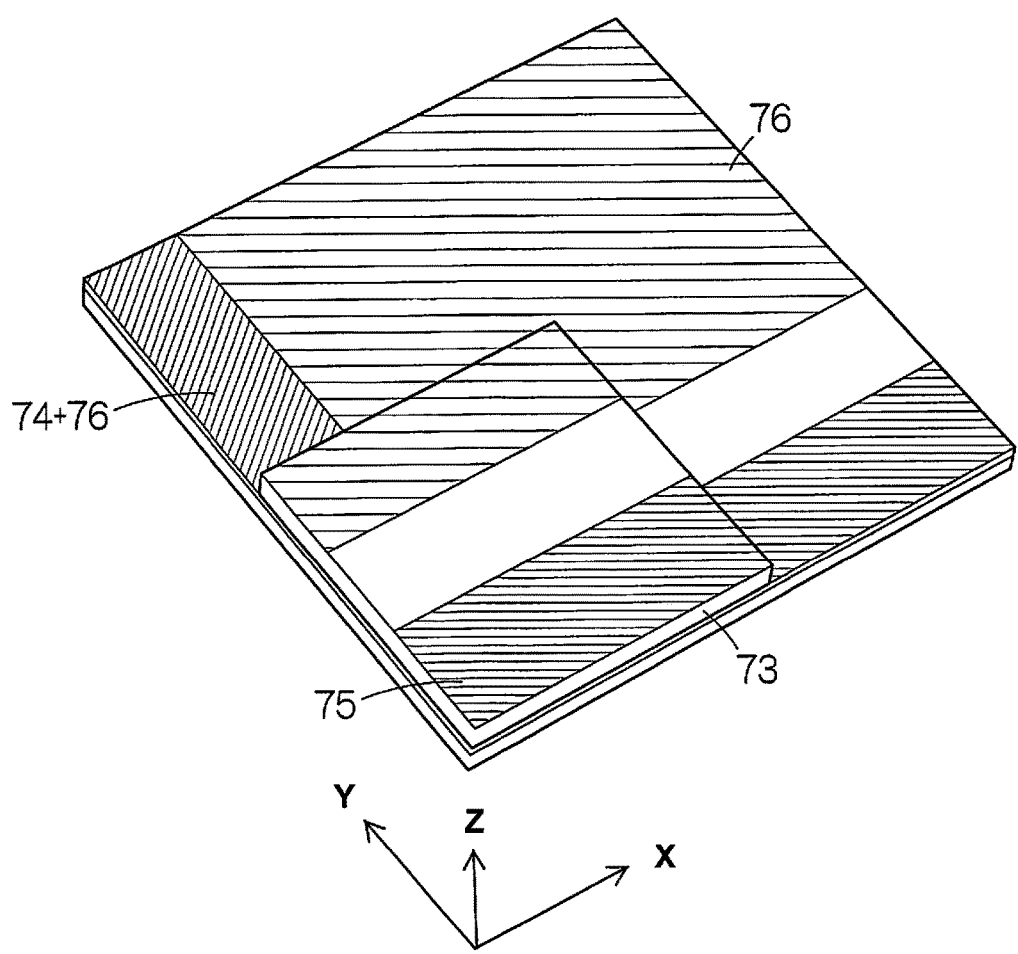
FIG. 5 is a diagram showing the simulation model that is configured on a piece of simulation software.

The inventors observe the behavior of the thin-film ultrasonic transducer element during transmission and during reception. In the observation, a distortion simulation with respect to the elements 23 is performed. As shown in FIG. 4, a simulation model 71 is configured so as to correspond to the element 23. In this simulation model 71, a vibration plate 72 is demarcated by the outline of the opening 48. The vibration plate 72 is formed to have a square shape, where one side=39.5 μm, when viewed from above. A piezoelectric film 73 is formed on the vibration plate 72. The outline of the piezoelectric film 73 is formed to have a square shape, where one side=31.5 μm, when viewed from above. Prior to the formation of the piezoelectric film 73, a bottom electrode 74 is laminated on the vibration plate 72. The piezoelectric film 73 is laminated on the bottom electrode 74. A top electrode 75 is laminated on the piezoelectric film 73. Electrically conductive films 76 (corresponding to the above-described second electrically conductive films 58) for moisture-proofing are formed of the material for the top electrode 75. The electrically conductive films 76 covered the piezoelectric film 73. As shown in FIGS. 4 and 5, to perform calculation processing, the simulation model 71 is equally divided into four portions when viewed from above (as shown by the dot-dash lines in FIG. 4). During transmission, a voltage of −15 V is applied to the top electrode 75. During reception, a pressure of $1 \times 10^5$ (Pa) is applied to the vibration plate 72 from vertically above. At that time, a distortion ε directly under the top electrode 75 and the electrically conductive films 76 is calculated.

Figure 6A:
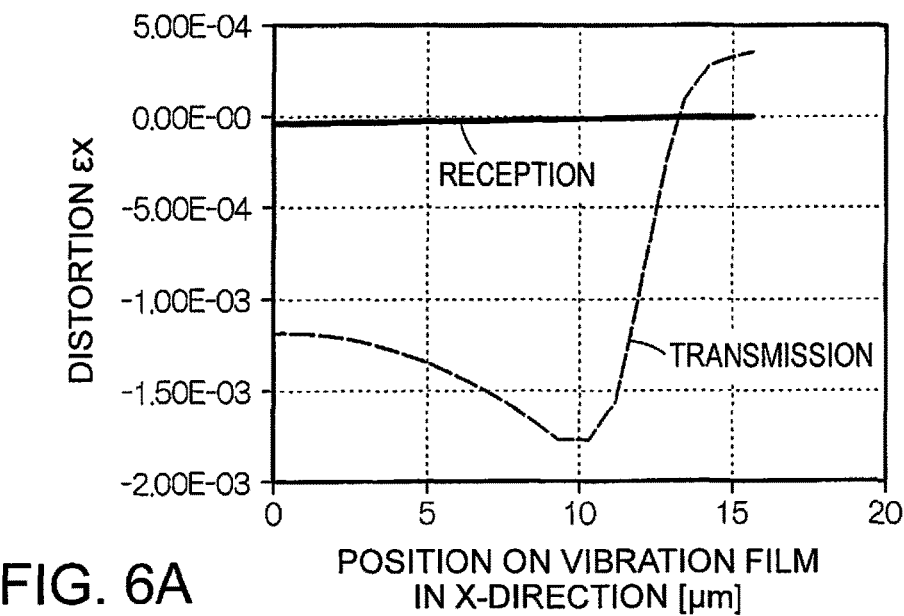
FIGS. 6A and 6B are graphs each showing distributions of distortion ε in an x-direction during transmission and during reception.
Figure 6B:
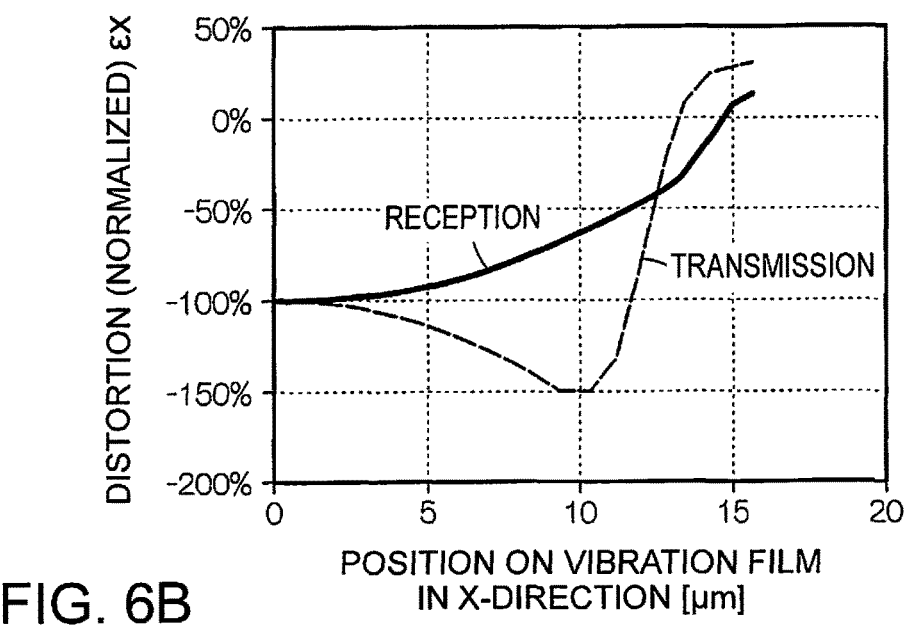
Figure 7A:
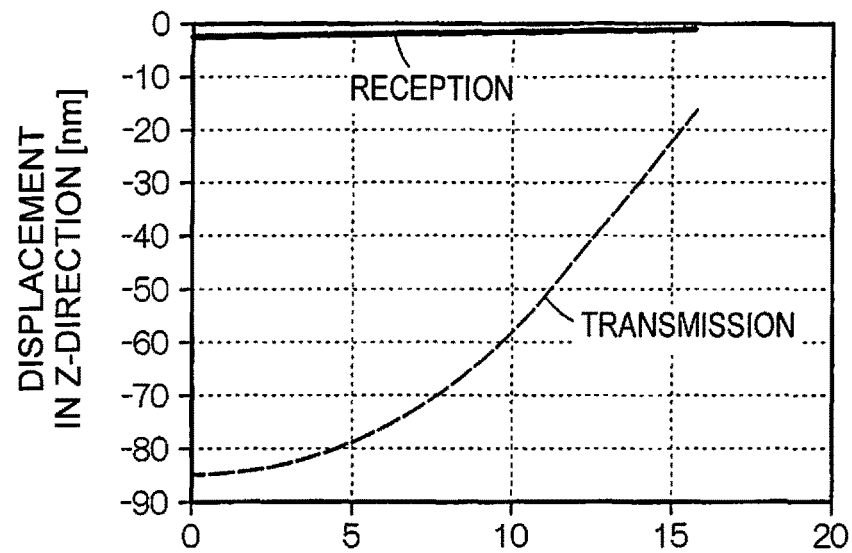
FIGS. 7A and 7B are graphs each showing distributions of z-direction displacement in the x-direction during transmission and during reception.
Figure 7B:
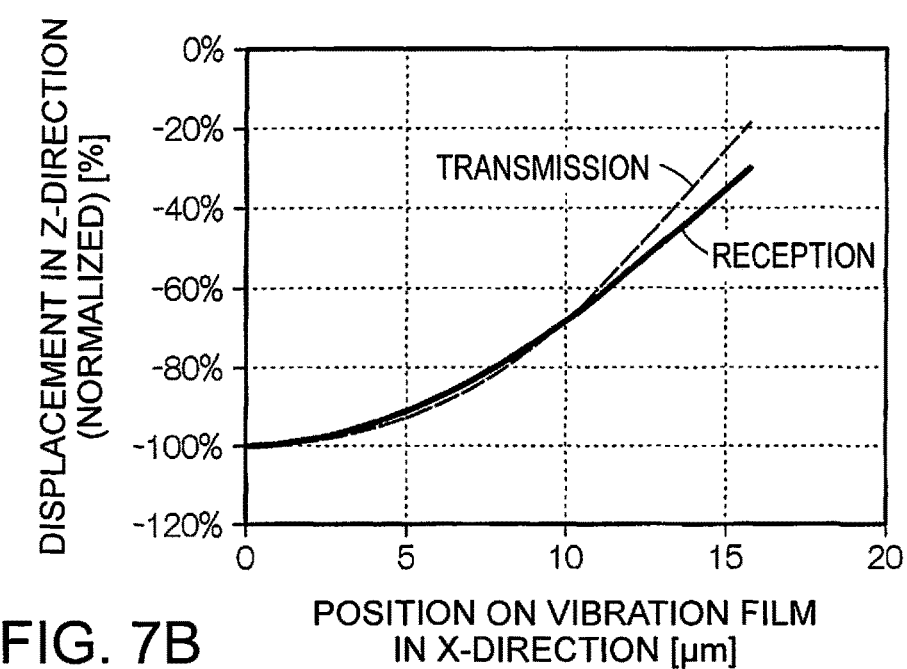
Figure 8A:
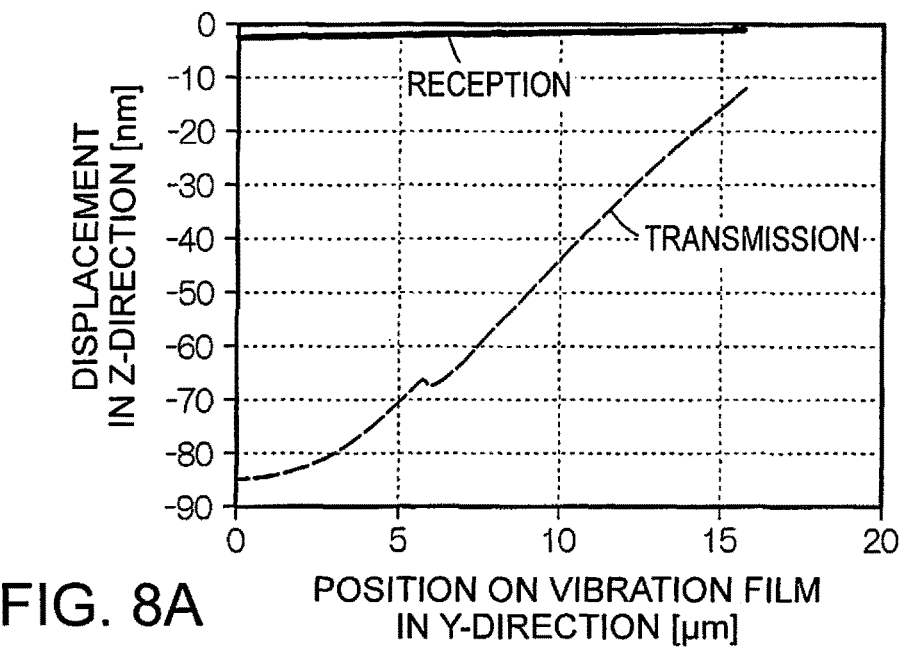
FIGS. 8A and 8B are graphs each showing distributions of z-direction displacement in a y-direction during transmission and during reception.
Figure 8B:
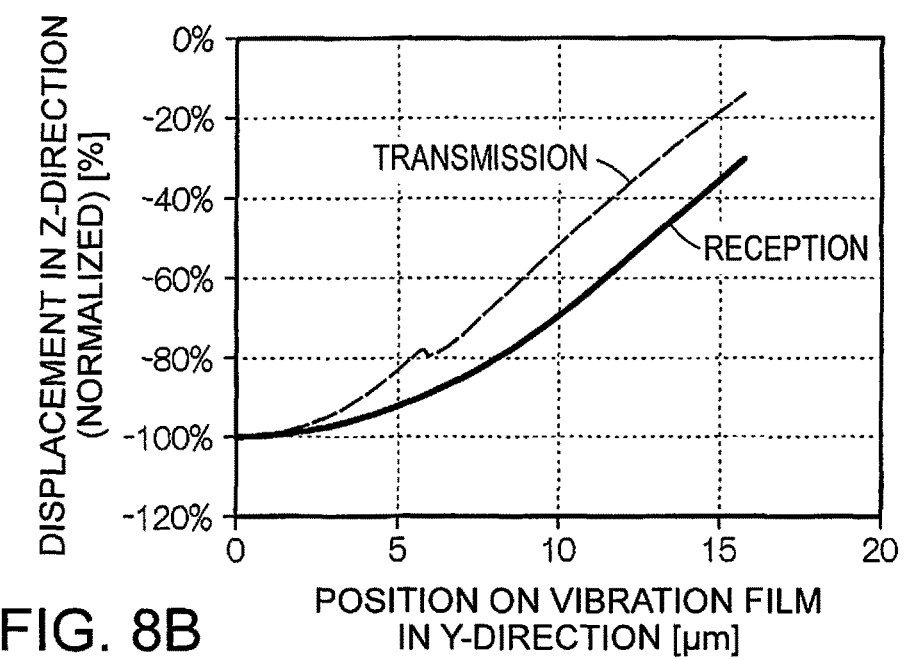

FIGS. 6A and 6B show distributions of the distortion ε in an x-direction. In each of FIGS. 6A and 6B, the origin of the horizontal axis corresponds to the center of the vibration plate 72. As a result of the distortion simulation, it is confirmed that with the same simulation model 71 being used during transmission and during reception, the distributions of the distortion ε during transmission and during reception are completely different from each other. It is confirmed that the absolute magnitude of distortion ε during transmission is significantly larger than that during reception. During transmission, a peak of the distortion ε occurred at a position that is away from the center of the vibration plate 72 toward an edge of the vibration plate 72, whereas during reception, a peak occurred at the center of the vibration plate 72. During reception, the distortion gradually increases from the edge of the vibration plate 72 toward the center of the vibration plate 72. During transmission, a compressive distortion ε is observed at the center of the vibration plate 72, and a tensile distortion ε is observed at a position near the edge of the vibration plate 72. FIGS. 7A and 7B show distributions of z-direction displacement in the x-direction. FIGS. 8A and 8B show distributions of z-direction displacement in a y-direction. In each of FIGS. 7A-8B, the origin of the horizontal axis corresponds to the center of the vibration plate 72. In each case, it is confirmed that the absolute magnitude of z-direction displacement during transmission is significantly larger than that during reception. It is made clear that optimum structures of the thin-film ultrasonic transducer element during transmission and during reception are different from each other.

Figure 9:
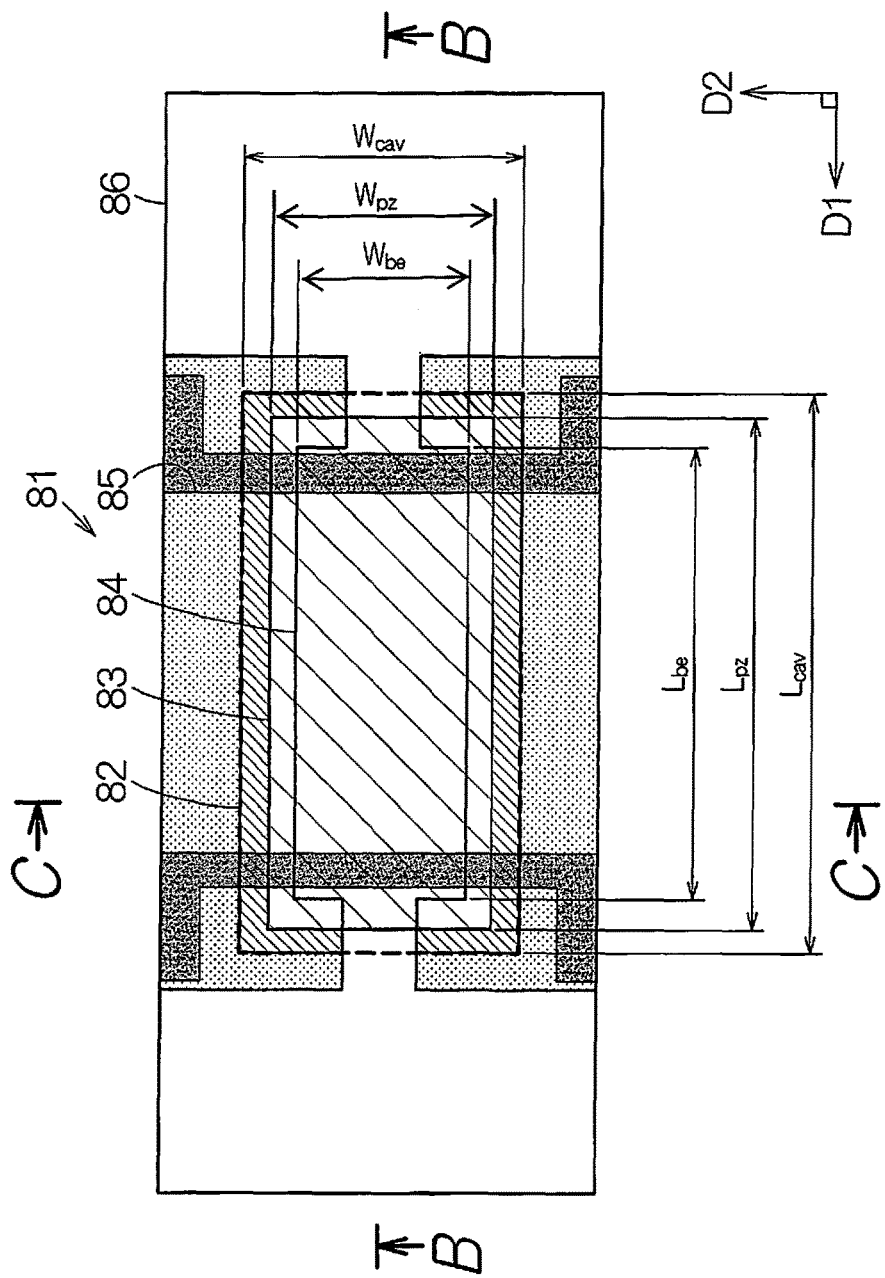
FIG. 9 is a conceptual diagram schematically showing the configuration of a simulation model.
Figure 10:
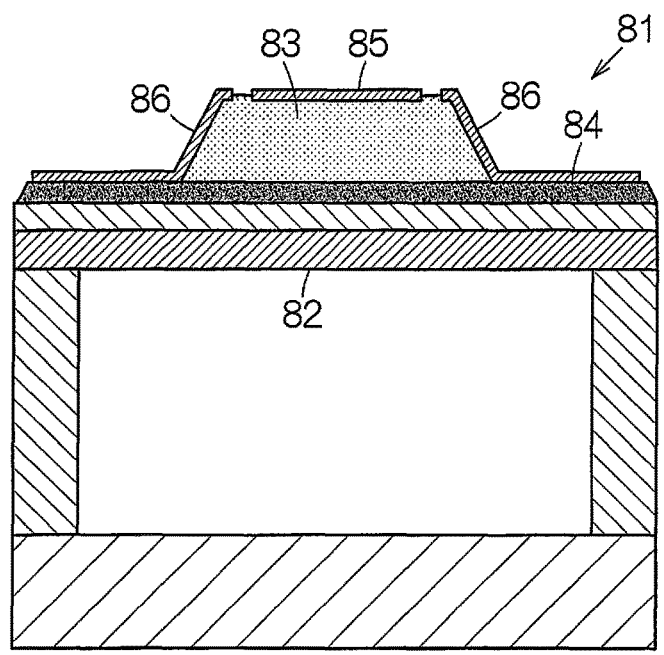
FIG. 10 is a cross-sectional view taken along line B-B in FIG. 9.

The inventors pursued a structure of the thin-film ultrasonic transducer element that is effective during reception. A displacement simulation with respect to the elements 23 is performed. A finite element analysis system, femtet (registered trademark), is used for the simulation. As shown in FIG. 9, a simulation model 81 is configured so as to correspond to an element 23. In this simulation model 81, a vibration plate 82 is demarcated by the outline of an opening 48. A piezoelectric film 83 is laminated on the vibration plate 82. Prior to the formation of the piezoelectric film 83, a bottom electrode 84 is laminated on the vibration plate 82. The piezoelectric film 83 is laminated on the bottom electrode 84. A top electrode 85 is formed on the piezoelectric film 83. Electrically conductive films 86 (corresponding to the above-described second electrically conductive films 58) for moisture-proofing are formed of the material for the top electrode 85. As shown in FIG. 10, the electrically conductive films 86 partially covered the piezoelectric film 83.

Figure 11:
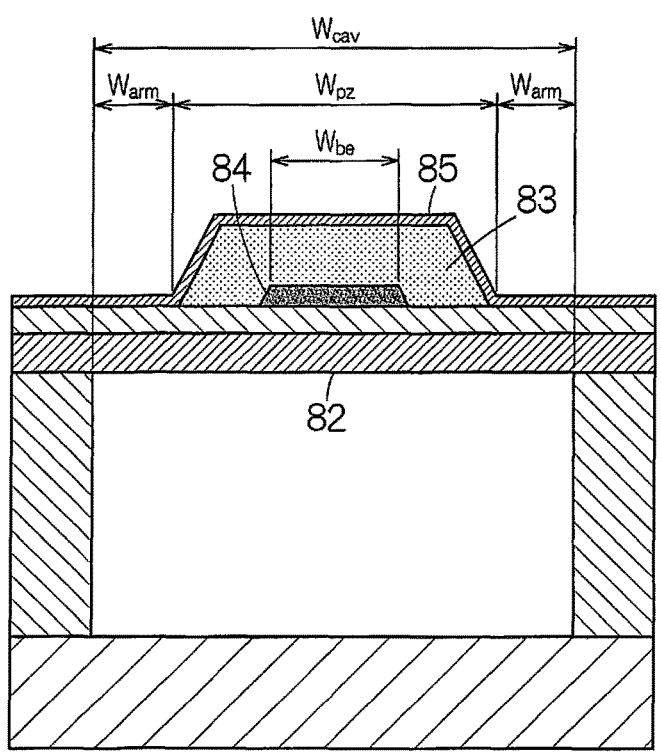
FIG. 11 is a cross-sectional view taken along line C-C in FIG. 9.

The bottom electrode 84 extends along the surface of the vibration plate 82 in a first direction D1 so as to have a length Lbe. The bottom electrode 84 has a width Wbe along the surface of the vibration plate 82 in a second direction D2 that is orthogonal to the first direction D1. The piezoelectric film 83 extends in the first direction D1 so as to have a length Lpz, and has a width Wpz in the second direction D2. The vibration plate 82 extends in the first direction D1 so as to have a length Lcav, and has a width Wcav in the second direction D2. Here, the aspect ratio Lcav/Wcav of the vibration plate 82 is set at 2. As shown in FIG. 11, an arm width Warm is defined beginning from the outline of the piezoelectric film 83 and extending along the second direction D2 to the outline of the vibration plate 82.

To perform the calculation processing, in the simulation model, the width Wpz of the piezoelectric film 83 is fixed.

Figure 12:
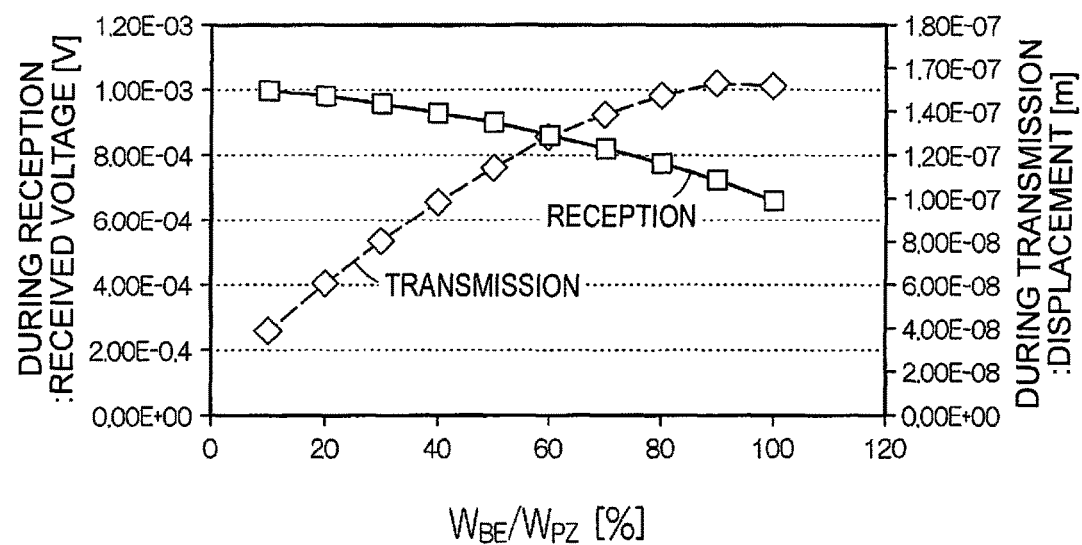
FIG. 12 is a graph showing "displacement during transmission" and "generated voltage during reception" in accordance with a change in ratio Wbe/Wpz.

The ratio Wbe/Wpz is changed by changing the width Wbe of the bottom electrode 84. "Displacement during transmission" and "generated voltage during reception" are calculated. During reception, a pressure of 1 (kPa) is vertically applied to the vibration plate 82. During transmission, a voltage of 10 (V) is applied to the bottom electrode 84. Here, the ratio Wpz/Wcav between the width Wpz of the piezoelectric film 83 and the width Wcav of the vibration plate 82 is fixed at 0.7. The width Wcav of the vibration plate 82 is fixed at 45 (μm). The ratio Warm/Wcav between the arm width Warm and the width Wcav of the vibration plate 82 is fixed at 0.15. As a result of the calculation processing, it is confirmed that, as shown in FIG. 12, during reception, the smaller the ratio Wbe/Wpz (the thinner the width Wbe of the bottom electrode 84), the larger the generated voltage (receiving voltage). On the other hand, it is confirmed that during transmission, the larger the ratio Wbe/Wpz, the larger the displacement.

Figure 13A:
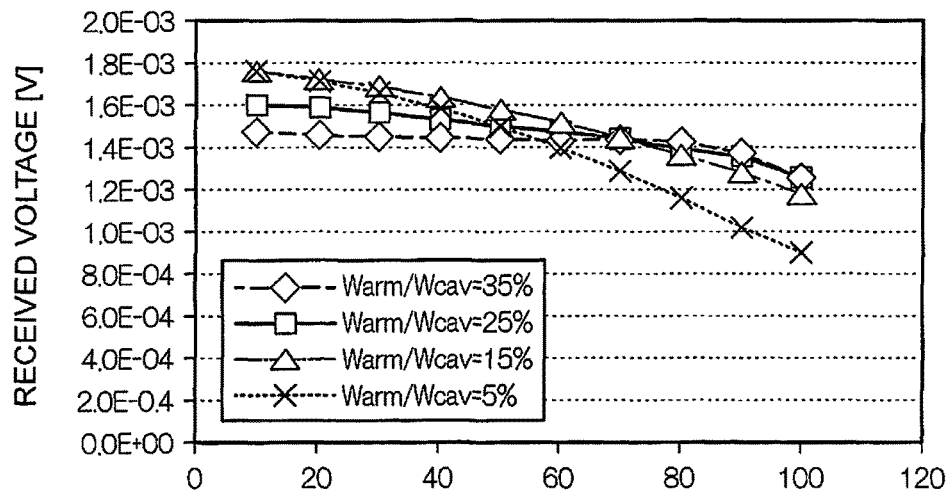
FIGS. 13A and 13B are graphs each showing "generated voltage during reception" that is generated in the simulation model when the width Wcav of a vibration plate is set at 60 (μm)
Figure 13B:
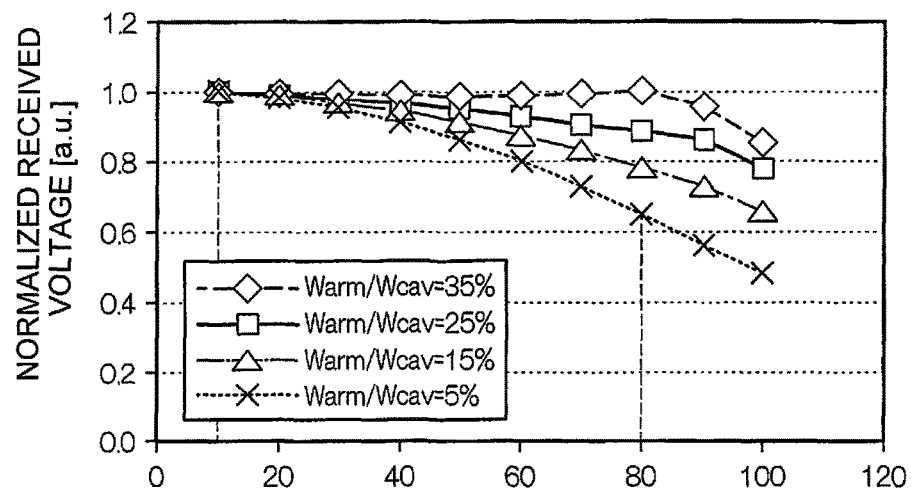
Figure 14A:
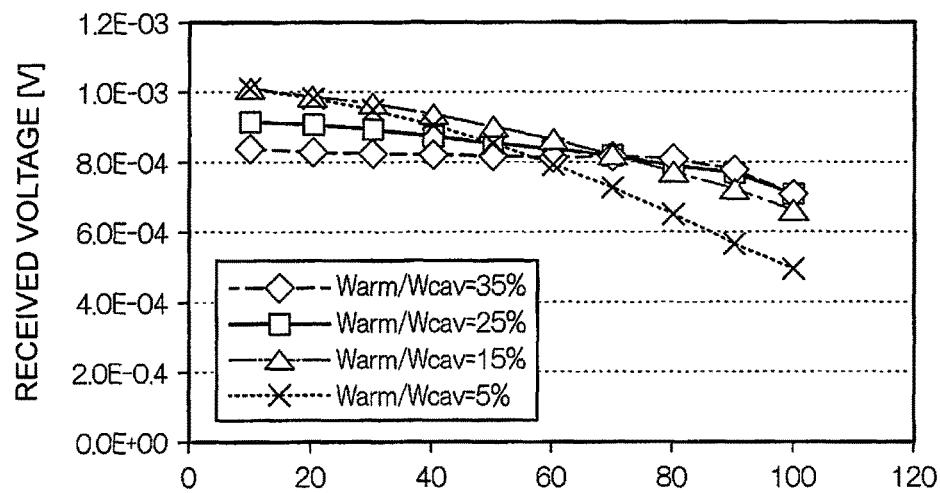
FIGS. 14A and 14B are graphs each showing "generated voltage during reception" that is generated in the simulation model when the width Wcav of the vibration plate is set at 45 (μm)
Figure 14B:
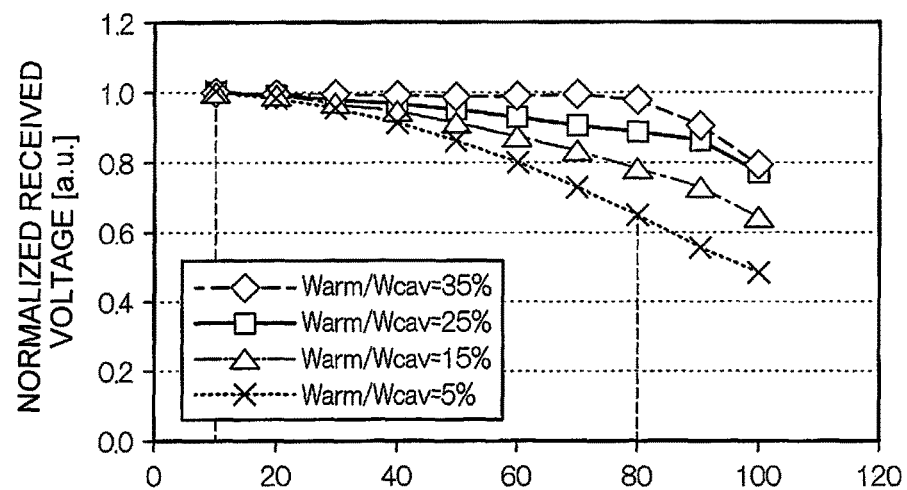
Figure 15A:
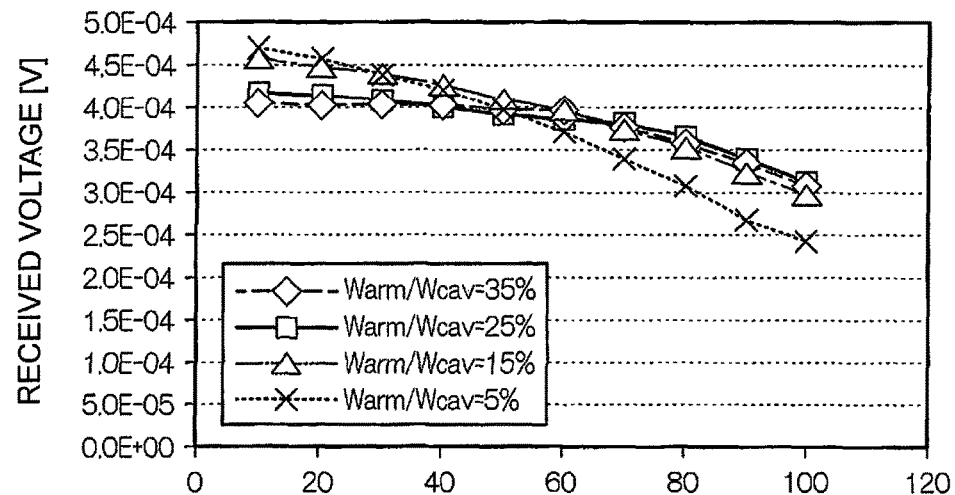
FIGS. 15A and 15B are graphs each showing "generated voltage during reception" that is generated in the simulation model when the width Wcav of the vibration plate is set at 30 (μm)
Figure 15B:
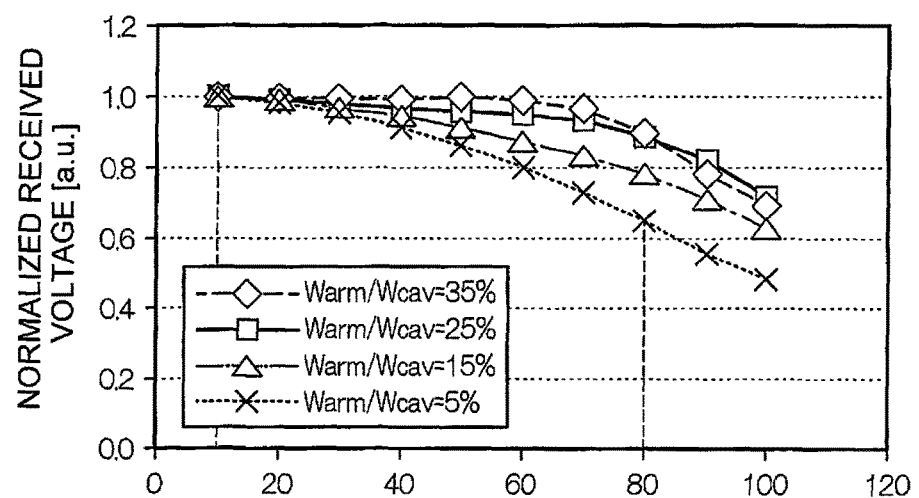
Figure 16A:
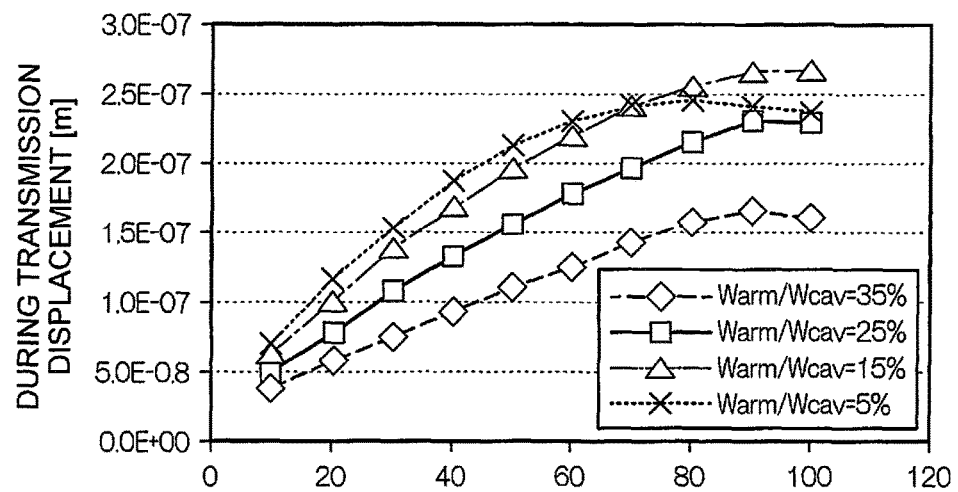
FIGS. 16A and 16B are graphs each showing "displacement during transmission" that is generated in the simulation model when the width Wcav of the vibration plate is set at 60 (μm)
Figure 16B:
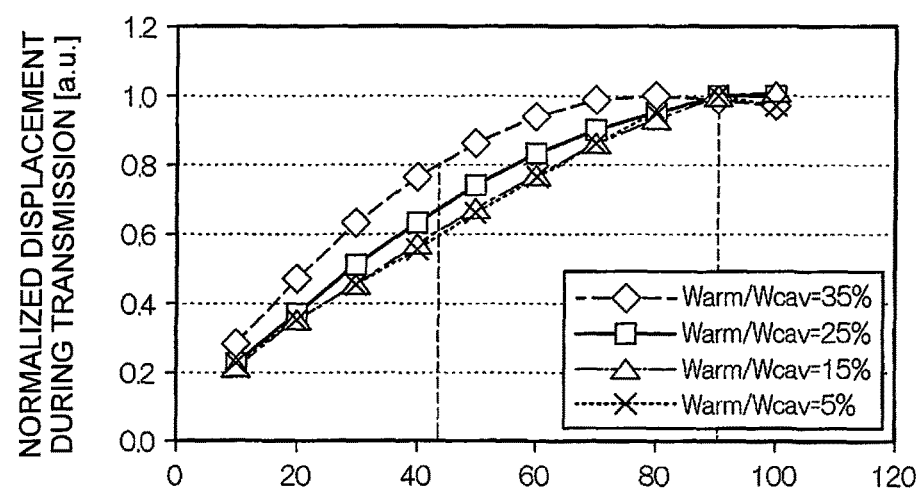
Figure 17A:
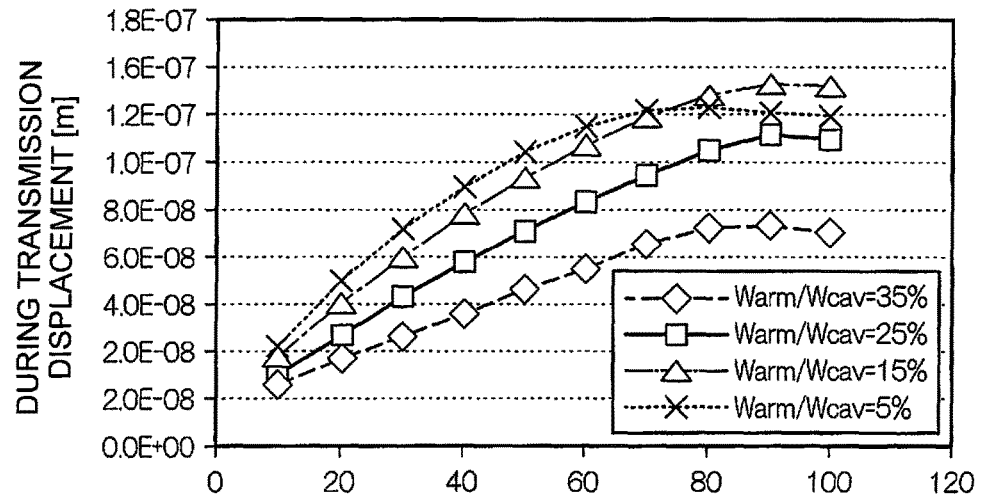
FIGS. 17A and 17B are graphs each showing "displacement during transmission" that is generated in the simulation model when the width Wcav of the vibration plate is set at 45 (μm)
Figure 17B:
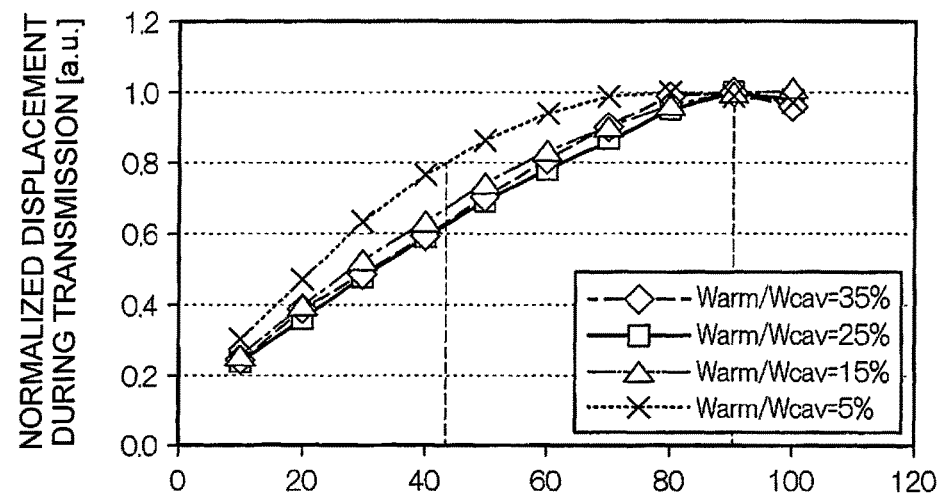
Figure 18A:
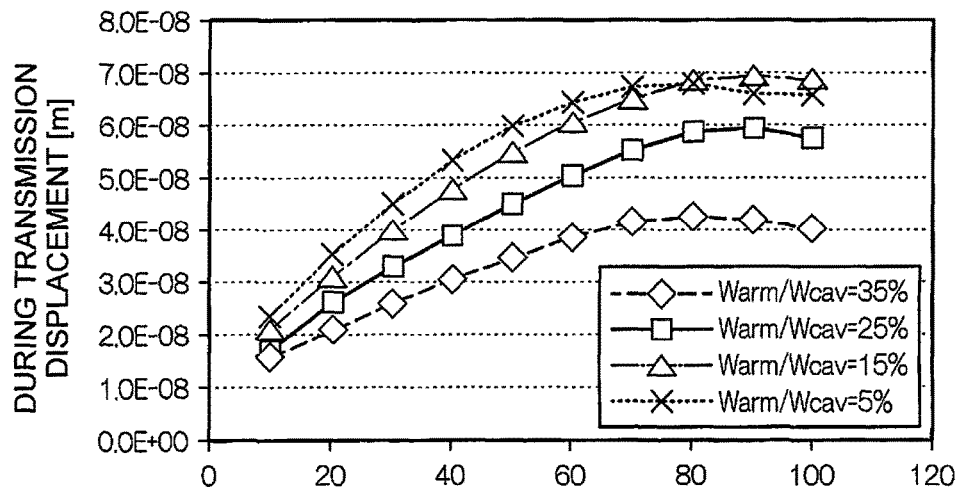
FIGS. 18A and 18B are graphs each showing "displacement during transmission" that is generated in the simulation model when the width Wcav of the vibration plate is set at 30 (μm)
Figure 18B:
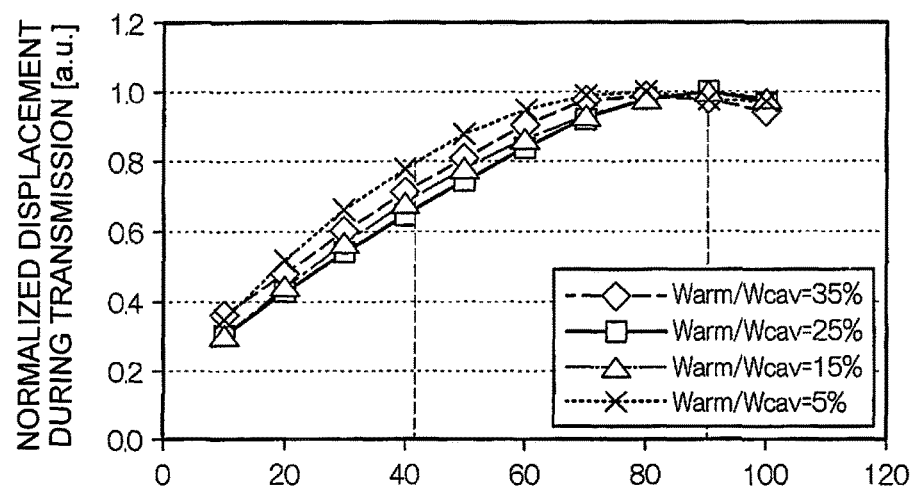

The inventors repeated the verification in the same manner while changing the width Wcav of the vibration plate 82 to a plurality of values. FIGS. 13A and 13B show "generated voltage during reception (receiving voltage)" that is generated in the simulation model 81 when the width Wcav of the vibration plate 82 is set at 60 (μm). FIGS. 14A and 14B show "generated voltage during reception (receiving voltage)" that is generated in the simulation model 81 when the width Wcav of the vibration plate 82 is set at 45 (μm). FIGS. 15A and 15B show "generated voltage during reception (receiving voltage)" that is generated in the simulation model 81 when the width Wcav of the vibration plate 82 is set at 30 (μm). In each case, the ratio Warm/Wcav between the arm width Warm and the width Wcav of the vibration plate 82 is changed to a plurality of values (0.35, 0.25, 0.15, and 0.05). Similarly, FIGS. 16A and 16B show "displacement during transmission" that is generated in the simulation model 81 when the width Wcav of the vibration plate 82 is set at 60 (μm). FIGS. 17A and 17B show "displacement during transmission" that is generated in the simulation model 81 when the width Wcav of the vibration plate 82 is set at 45 (μm). FIGS. 18A and 18B show "displacement during transmission" that is generated in the simulation model 81 when the width Wcav of the vibration plate 82 is set at 30 (μm). In FIGS. 13B, 14B, 15B, 16B, 17B, and 18B, and the following FIGS. 20A, 20B, 21A, 21B, 25B, 27, and 29B, the "a.u." is an abbreviation for "arbitrary unit."

As described above, when ultrasonic waves act on the vibration plate 82, the vibration plate 82 vibrates. A distortion is generated in the piezoelectric film 83 in accordance with the vibration of the vibration plate 82. The distortion in the piezoelectric film 83 generates a voltage. The generated voltage is extracted from the bottom electrode 84 and the top electrode 85. In this manner, the ultrasonic waves are detected. If the ratio Wbe/Wpz between the width Wbe of the bottom electrode 84 and the width Wpz of the piezoelectric film 83 is set to be not less than 0.1 and not more than 0.8, a sufficient generated voltage during reception can be secured. On the other hand, if the ratio Wbe/Wpz is less than 0.1, the electric resistance of the bottom electrode 84 increases. If the ratio Wbe/Wpz is more than 0.8, in some cases, the voltage becomes lower than 60% of the maximum voltage value, and the generated voltage is thus outside the usage range. In particular, during reception, when the ratio Warm/Wcav is set at 0.35, the change in the generated voltage remains small irrespective of the change in the ratio Wbe/Wpz, and the more the ratio Warm/Wcav is reduced, the larger the change in the generated voltage in accordance with the change in the ratio Wbe/Wpz. If the ratio Wbe/Wpz is not more than 0.5, received voltages, namely generated voltages during reception, which are larger than those when the ratio Warm/Wcav is 0.35, are secured irrespective of the change in the ratio Warm/Wcav. Therefore, it is understood that if the ratio Wbe/Wpz is not more than 0.5, a favorable generated voltage is obtained even when a condition changes.

Figure 19:
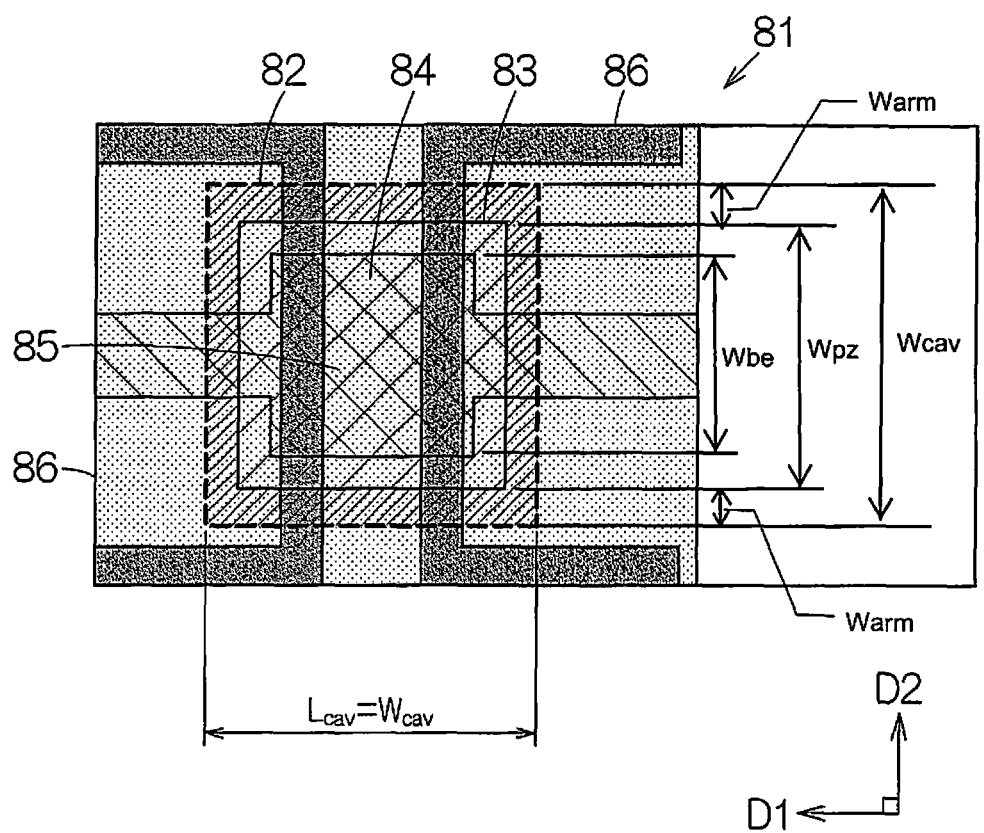
FIG. 19 is a conceptual diagram schematically showing a simulation model having an aspect ratio Lcav/Wcav of 1.
Figure 20A:
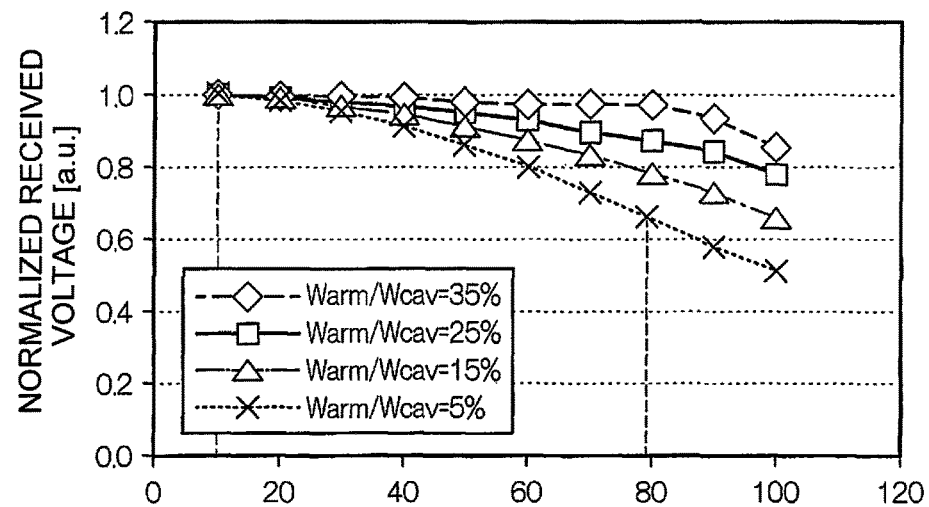
FIGS. 20A and 20B are graphs each showing normalized "generated voltage during reception" that is generated in the simulation model when the aspect ratio Lcav/Wcav is 1 or 2.
Figure 20B:
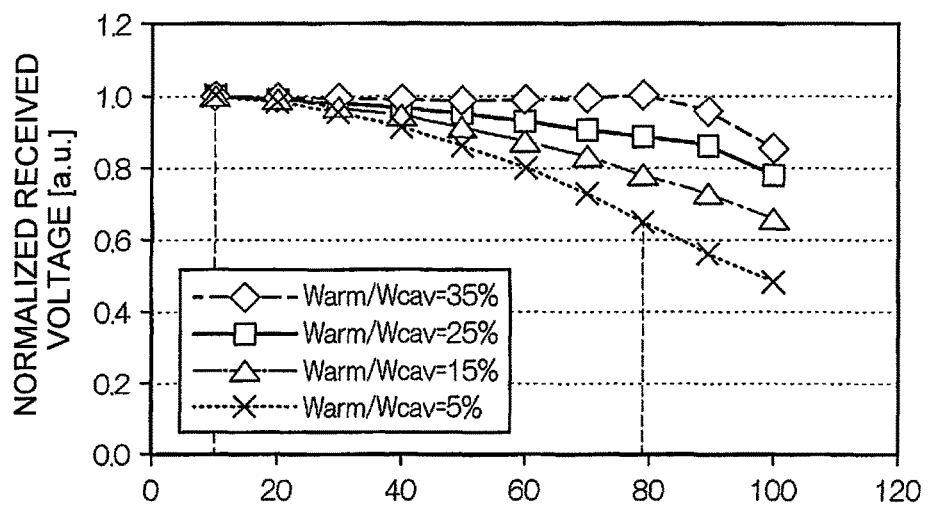
Figure 21A:
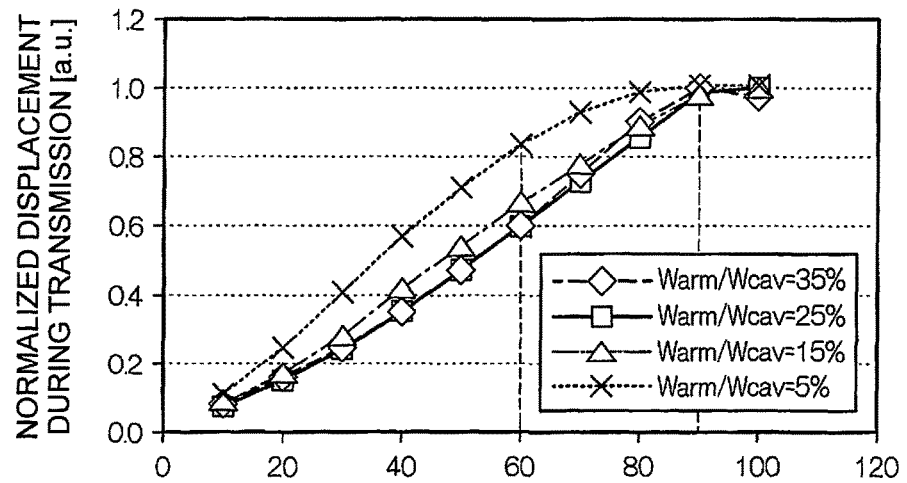
FIGS. 21A and 21B are graphs each showing normalized "displacement during transmission" that is generated in the simulation model when the aspect ratio Lcav/Wcav is 1 or 2.
Figure 21B:
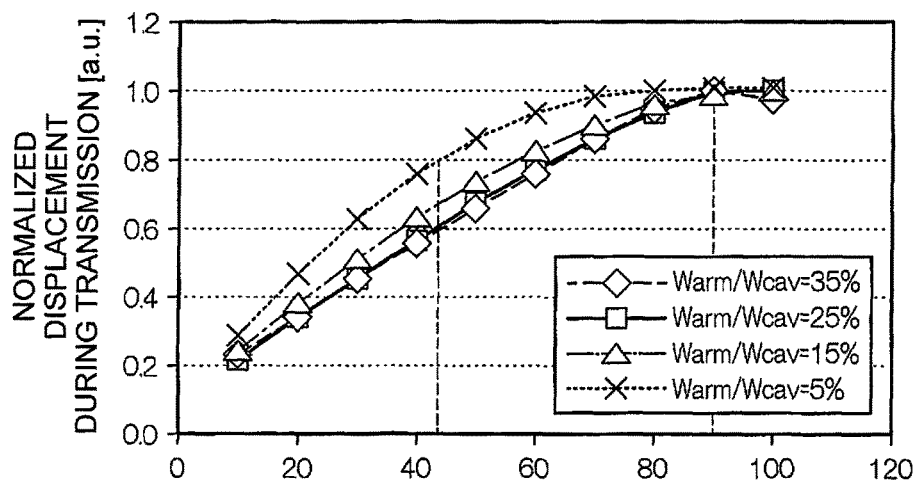
Figure 22:
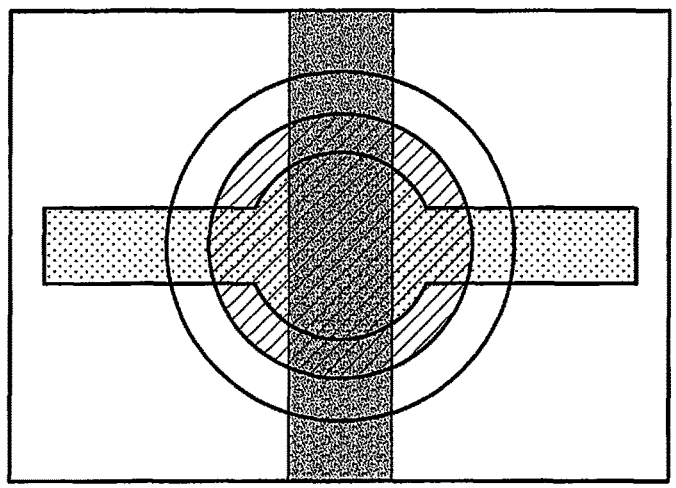
FIG. 22 is a conceptual diagram schematically showing a simulation model with a vibration plate having a circular outline.
Figure 23:
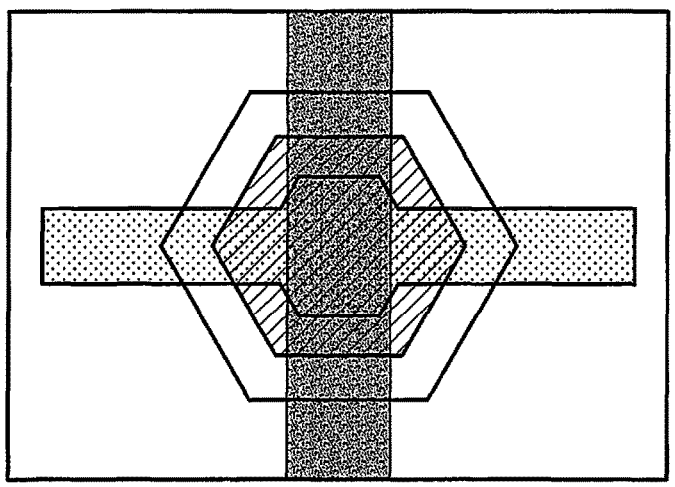
FIG. 23 is a conceptual diagram schematically showing a simulation model with a vibration plate having a hexagonal outline.
Figure 24:
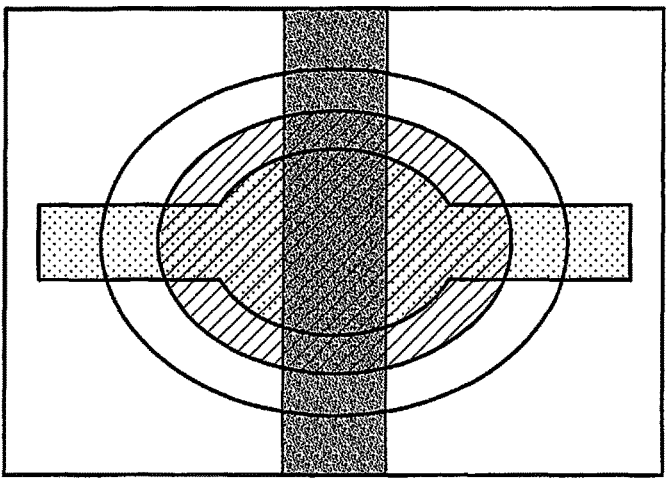
FIG. 24 is a conceptual diagram schematically showing a simulation model with a vibration plate having an elliptical outline.

The inventors performed a verification in the same manner while changing the shape of the vibration plate 82 when viewed from above. As shown in FIG. 19, based on the simulation model 81, the inventors set the aspect ratio Lcav/Wcav of the vibration plate 82 at 1. As shown in FIGS. 20A and 20B, during reception, in both of the cases where the aspect ratio is 1 and where the aspect ratio is 2, the same tendencies are observed. Similarly, as shown in FIGS. 21A and 21B, during transmission as well, the same tendencies are observed when the aspect ratio is 1 and when the aspect ratio is 2. Even when the shape of the outline of the vibration plate 82 is changed to a circular shape, a hexagonal shape, or an elliptical shape as shown in FIGS. 22 to 24, the same tendencies are observed.

Figure 25A:
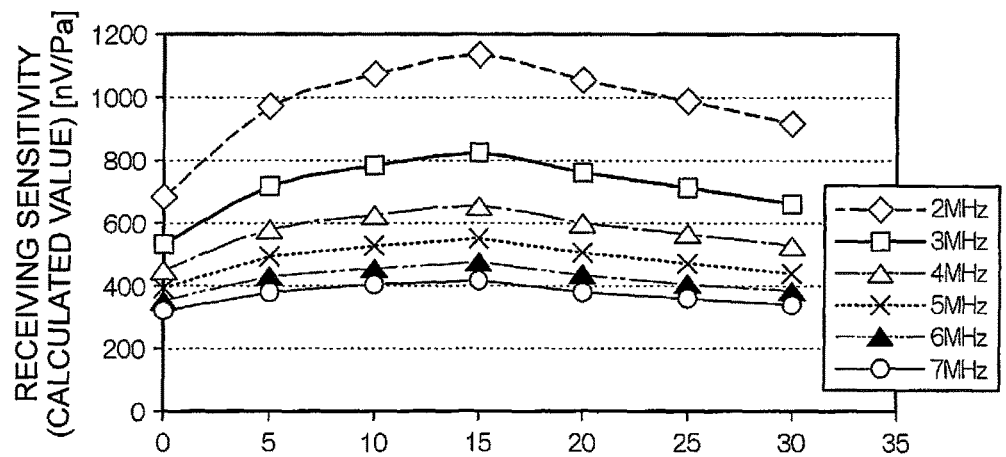
FIGS. 25A and 25B are graphs each showing "generated voltage during reception" in accordance with a change in ratio Warm/Wcav.
Figure 25B:
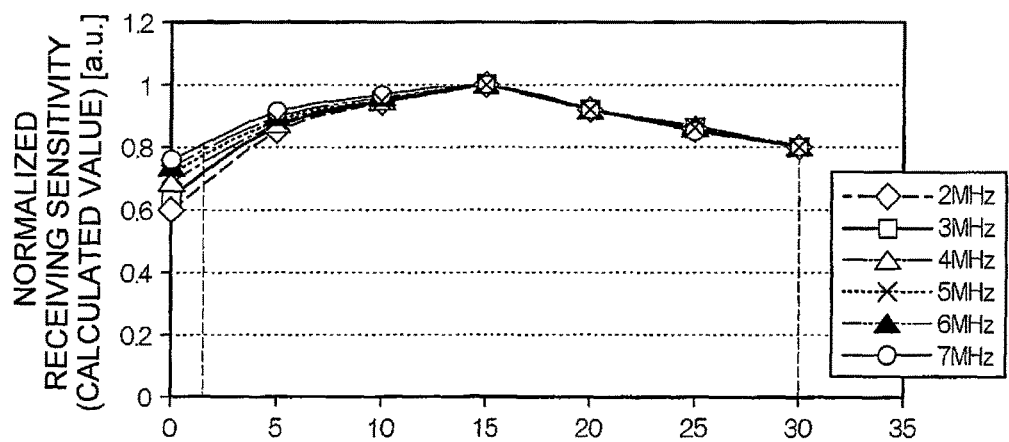

Next, the inventors performed a verification in the same manner while changing the ratio Warm/Wcav between the arm width Warm and the width Wcav of the vibration plate 82 as shown in FIG. 19. The aspect ratio Lcav/Wcav of the vibration plate 82 is set at 2. The width Wbe of the bottom electrode 84 is set to be a width smaller than the width Wpz of the piezoelectric film 83 by 8 μm. The width Wcav of the vibration plate 82 is set for each value of the ratio Warm/Wcav such that a constant resonance frequency is maintained. Otherwise, the resonance frequency increases as the arm width Warm decreases, and thus fair comparison of generated voltages during reception cannot be performed. As a result of calculation processing, as shown in FIGS. 25A and 25B, whether the resonance frequency is high or low, peak values of the generated voltage are observed when the ratio Warm/Wcav is about 0.15. When 0.8 times the maximum generated voltage is defined as a usage range, it is understood that an improvement in reception characteristics can be expected if the ratio Warm/Wcav is set to be not less than 0.02 and not more than 0.3.

Figure 26:
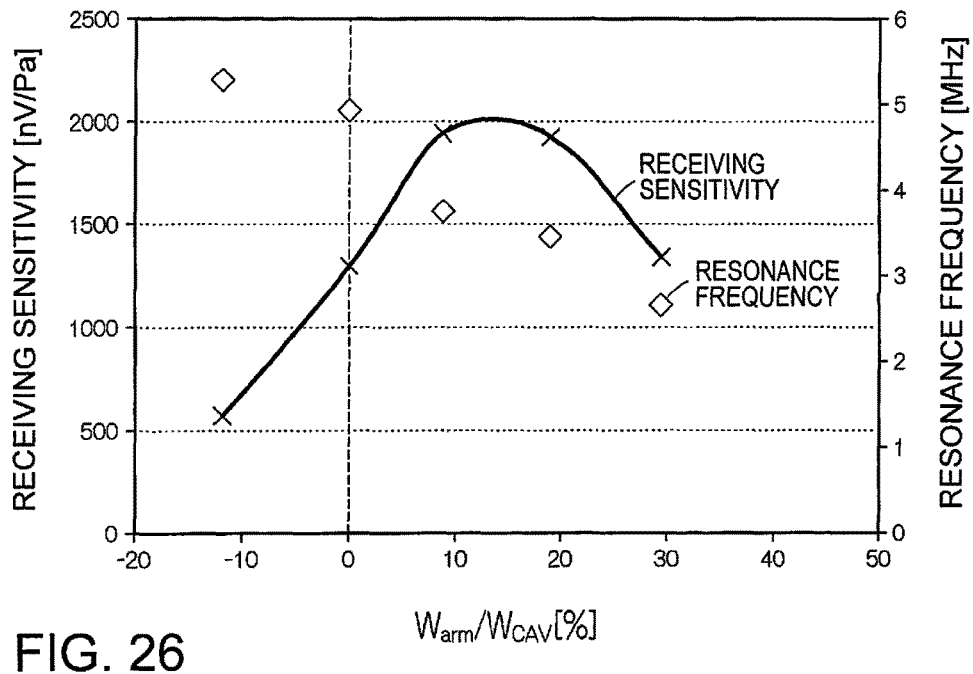
FIG. 26 is a graph showing a relationship between the ratio Warm/Wcav and the resonance frequency based on actual measurement.
Figure 27:
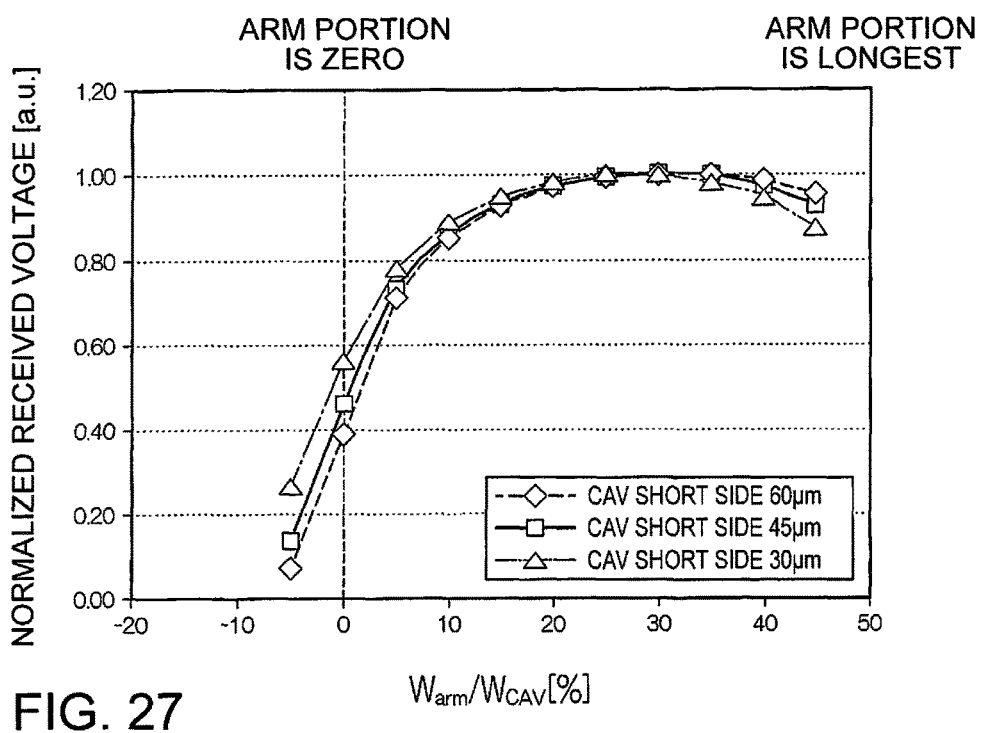
FIG. 27 is a graph showing a relationship between the ratio Warm/Wcav and the generated voltage during reception based on a simulation.

The inventors actually measured the receiving sensitivity in accordance with the ratio Warm/Wcav between the arm width Warm and the width Wcav of the vibration plate 82. The aspect ratio Lcav/Wcav of the vibration plate 82 is set at 10. The width Wcav of the vibration plate 82 is maintained constant. As shown in FIG. 26, the resonance frequency tended to increase as the arm width Warm decreased. As a result of the actual measurement, a peak value of the generated voltage is observed when the ratio Warm/Wcav is about 0.1 to 0.2. Similarly, the inventors performed a simulation. As shown in FIG. 27, peak values of the generated voltage are observed when the ratio Warm/Wcav is about 0.2 to 0.3.

Figure 28:
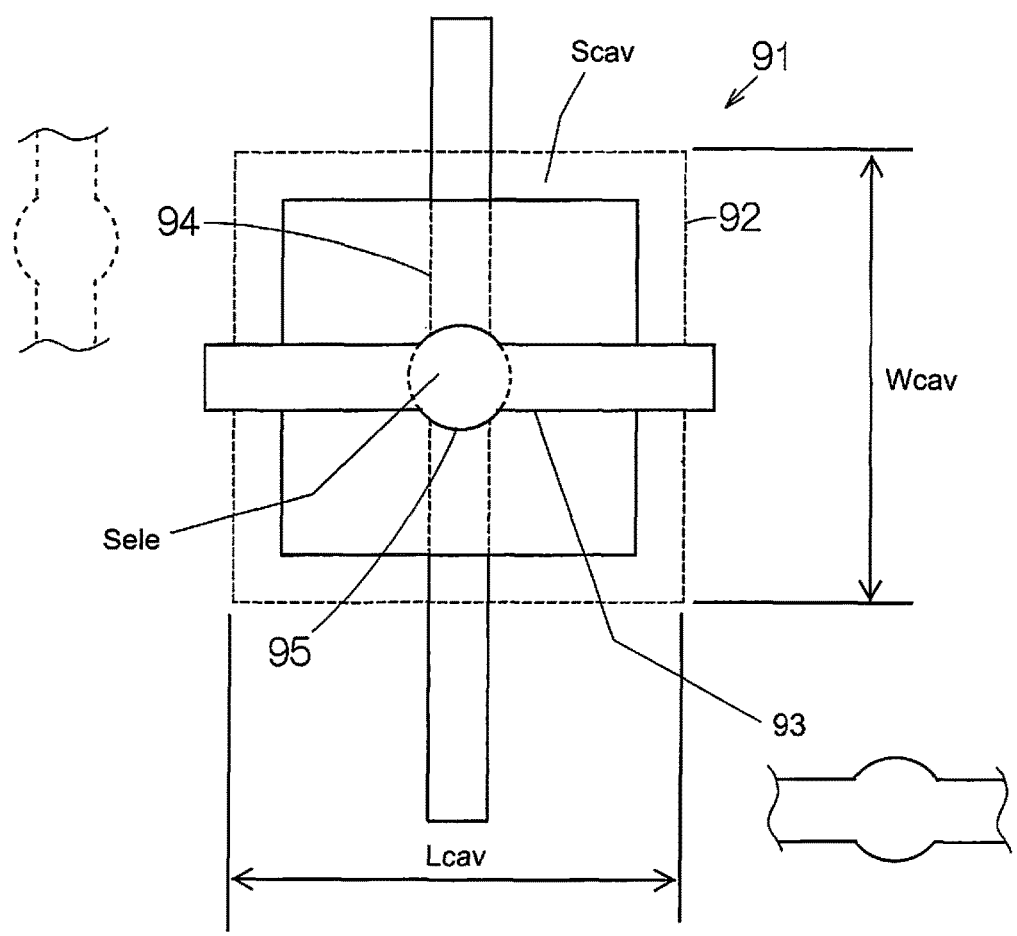
FIG. 28 is a conceptual diagram schematically showing a simulation model in which an extent of overlap between a top electrode and a bottom electrode is defined.
Figure 29A:
FIGS. 29A and 29B are graphs each showing a relationship between the extent of overlap between the top electrode and the bottom electrode and the generated voltage during reception based on a simulation.
Figure 29B:
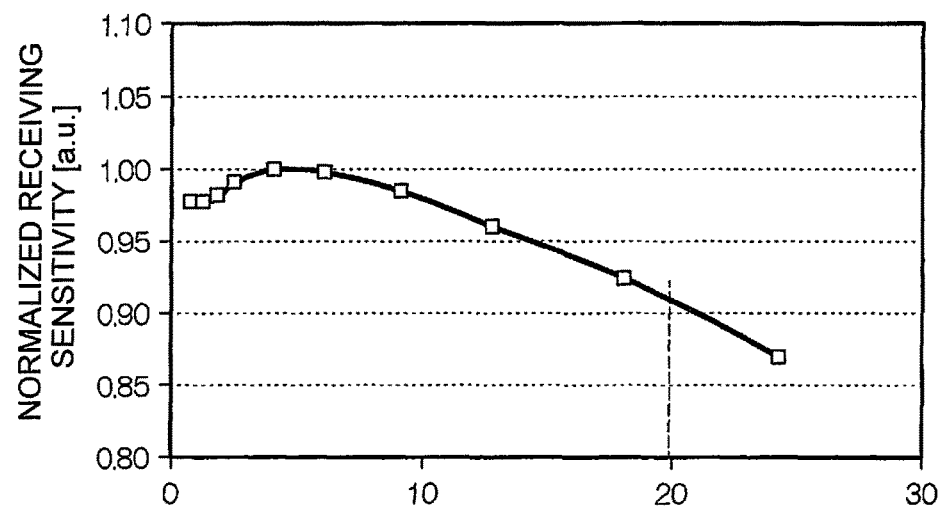

Next, the inventors perform a verification in the same manner while changing the extent of overlap between the top electrode and the bottom electrode in a plan view that is orthogonal to the surface of the vibration plate. As shown in FIG. 28, based on a simulation model 91, the inventors set the aspect ratio Lcav/Wcav of a vibration plate 92 at 1. To set the extent of overlap, a partial piezoelectric body (hereinafter referred to as "intersecting portion") 95 is defined, the intersecting portion 95 being sandwiched between a top electrode 93 and a bottom electrode 94 and having a circular outline. The diameter of the intersecting portion 95 is used as a parameter. The center of the intersecting portion 95 is superposed on the center of gravity of the vibration plate 92 as viewed in FIG. 28. The size of each side of the outline of the vibration plate 92 is set at 39.5 µm. As shown in FIGS. 29A and 29B, when 0.9 or more times the normalized receiving sensitivity is defined as a usage range, it is understood that a high receiving sensitivity can be obtained if the area Sele of the intersecting portion 95 is not less than 1% and not more than 20% with respect to the area Scav of the vibration plate 92 in a plan view that is orthogonal to the surface of the vibration plate 92 (as viewed in FIG. 28). However, although the size of each side is set at 39.5 µm in this verification, the same results can be obtained if the size of each side is within a range of not less than 20 µm and not more than 100 µm.

In the above-described verifications, the film thickness of the silicon oxide layer 51 of the vibration plate is set at 1070 nm; however, an effective effect can be achieved if this film thickness is within a range of not less than 1000 nm and not more than 5000 nm. Although the film thickness of the piezoelectric film 55 is set at 1350 nm, an effective effect can be achieved if this film thickness is within a range of not less than 500 nm and not more than 3000 nm. Although the film thickness of the bottom electrodes 74, 84, and 94 is set at 150 nm, an effective effect can be achieved if this film thickness is within a range of not less than 50 nm and not more than 500 nm. Although the film thickness of the top electrodes 75, 85, and 93 is set at 50 nm, an effective effect can be achieved if this film thickness is within a range of not less than 10 nm and not more than 100 nm.

Although some embodiments of the invention have been described in detail above, a person skilled in the art will readily understand that various modifications may be made without substantially departing from the novel teachings and the effects of the invention. Therefore, such modifications are entirely included within the scope of the invention. For example, any term described at least once together with a broader or synonymous different term in the specification or the drawings may be replaced by the different term at any place in the specification or the drawings. Moreover, the configurations and operations of the ultrasonic diagnostic apparatus 11, the ultrasonic probe 13, the ultrasonic device 17, and the like are not limited to those described in the foregoing embodiments, but may be modified in various manners.

According to at least one aspect of the embodiments, it is possible to provide an ultrasonic sensor that enables a sufficient generated voltage during reception to be secured in accordance with adjustment of the width of a bottom electrode.

An aspect of the embodiments is directed to an ultrasonic sensor including a vibration plate, a bottom electrode that is laminated on the vibration plate, that has a length L along a surface of the vibration plate in a first direction, and that has a width Wbe along the surface of the vibration plate in a second direction that is orthogonal to the first direction, the width Wbe being not more than the length L, a piezoelectric body that is laminated on the bottom electrode and that has a width Wpz in the second direction, and a top electrode that is laminated on the piezoelectric body, wherein a ratio Wbe/Wpz between the width Wbe of the bottom electrode and the width Wpz of the piezoelectric body is not less than 0.1 and not more than 0.8.

When ultrasonic waves act on the vibration plate, the vibration plate vibrates. A distortion is generated in the piezoelectric body in accordance with the vibration of the vibration plate. The distortion in the piezoelectric body generates a voltage. The generated voltage is extracted from the bottom electrode and the top electrode. In this manner, the ultrasonic waves are detected. Since the ratio Wbe/Wpz between the width Wbe of the bottom electrode and the width Wpz of the piezoelectric body is set to be not less than 0.1 and not more than 0.8, a sufficient generated voltage during reception can be secured. On the other hand, if the ratio Wbe/Wpz is less than 0.1, the electric resistance of the bottom electrode increases. If the ratio Wbe/Wpz is more than 0.8, in some cases, the voltage becomes lower than 60% of the maximum voltage value, and the generated voltage is thus outside the usage range.

It is preferable if the ratio Wbe/Wpz is not more than 0.5. A favorable generated voltage can be obtained even when a condition changes.

It is preferable if, in a plan view that is orthogonal to the surface of the vibration plate, a distance from an outline of the piezoelectric body to an outline of the vibration plate in the second direction is not less than 0.02 times and not more than 0.3 times a width of the vibration plate. A sufficient receiving sensitivity can be obtained.

It is also possible that in the first direction, the top electrode has a smaller area than the piezoelectric body. The piezoelectric body prevents short-circuiting of the top electrode with respect to the bottom electrode.

It is preferable if an aspect ratio Lcav/Wcav between a width Wcav of the vibration plate in the second direction and a length Lcav thereof in the first direction is not less than 1 and not more than 2. A sufficient receiving sensitivity can be obtained irrespective of the aspect ratio.

It is preferable if, in a plan view that is orthogonal to the surface of the vibration plate, an area of overlap between the top electrode and the bottom electrode is within a range of not less than 1% and not more than 20% with respect to an area of the vibration plate that is defined by the outline thereof in the plan view. With this setting, the receiving sensitivity can be increased.

It is also possible that the outline of the vibration plate has any of a circular shape, a hexagonal shape, and an elliptical shape. A sufficient receiving sensitivity can be obtained irrespective of the shape of the vibration plate.

The ultrasonic sensor can be used in a state in which it is incorporated into a probe. The probe can include the ultrasonic sensor and a housing that supports the ultrasonic sensor.

The ultrasonic sensor can be used in a state in which it is incorporated into an electronic apparatus. The electronic apparatus can include the ultrasonic sensor and a processing unit that is connected to the ultrasonic sensor and that processes an output from the ultrasonic sensor.

The ultrasonic sensor can be used in a state in which it is incorporated into an ultrasonic imaging apparatus. The ultrasonic imaging apparatus can include the ultrasonic sensor, a processing unit that is connected to the ultrasonic sensor and that processes an output from the ultrasonic sensor and generates an image, and a display device that displays the image.

The entire disclosure of Japanese Patent Application No. 2014-201934 filed on Sep. 30, 2014 is expressly incorporated by reference herein.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:
1. An ultrasonic sensor, comprising:
   a vibration plate;
   a first electrode laminated on the vibration plate, the first electrode having a length along a surface of the vibration plate in a first direction and a width Wbe along the surface of the vibration plate in a second direction that is orthogonal to the first direction, the width Wbe being not more than the length;
   a piezoelectric body that is laminated on the first electrode and that has a width Wpz in the second direction; and
   a second electrode laminated on the piezoelectric body,
   a ratio Wbe/Wpz between the width Wbe of the first electrode and the width Wpz of the piezoelectric body being not less than 0.1 and not more than 0.8.

2. The ultrasonic sensor according to claim 1, wherein the ratio Wbe/Wpz is not more than 0.5.
3. The ultrasonic sensor according to claim 1, wherein in a plan view that is orthogonal to the surface of the vibration plate, a distance from an outline of the piezoelectric body to an outline of the vibration plate in the second direction is not less than 0.02 times and not more than 0.3 times a width of the vibration plate.
4. The ultrasonic sensor according to claim 1, wherein in the first direction, the second electrode has a smaller width than the piezoelectric body.
5. The ultrasonic sensor according to claim 1, wherein an aspect ratio Lcav/Wcav between a width Wcav of the vibration plate in the second direction and a length Lcav of the vibration plate in the first direction is not less than 1 and not more than 2.
6. The ultrasonic sensor according to claim 1, wherein in a plan view that is orthogonal to the surface of the vibration plate, an area of overlap between the second electrode and the first electrode is within a range of not less than 1% and not more than 20% with respect to an area of the vibration plate that is defined by an outline of the vibration plate in the plan view.
7. The ultrasonic sensor according to claim 1, wherein an outline of the vibration plate has one of a circular shape, a hexagonal shape, and an elliptical shape.
8. A probe, comprising:
the ultrasonic sensor according to claim 1; and
a housing that supports the ultrasonic sensor.
9. An electronic apparatus, comprising:
the ultrasonic sensor according to claim 1; and
a processor connected to the ultrasonic sensor and configured to process an output from the ultrasonic sensor.
10. An ultrasonic imaging apparatus, comprising:
the ultrasonic sensor according to claim 1; and
a display device configured to display an image generated based on an output from the ultrasonic sensor.

* * * * *